United States Patent
Ziff et al.

(10) Patent No.: US 12,279,819 B1
(45) Date of Patent: Apr. 22, 2025

(54) VISION CORRECTION SIMULATION SYSTEM AND METHODS OF USE

(71) Applicant: VirtuaLens, LLC, Cedar Park, TX (US)

(72) Inventors: Matteo Oscar Ziff, Miami, FL (US); John William Branch, Cedar Park, TX (US)

(73) Assignee: VIRTUALENS LLC, Cedar Park, TX (US)

( * ) Notice: Subject to any disclaimer, the term of this patent is extended or adjusted under 35 U.S.C. 154(b) by 0 days.

(21) Appl. No.: 18/900,074

(22) Filed: Sep. 27, 2024

(51) Int. Cl.
*A61B 3/032* (2006.01)
*A61B 3/00* (2006.01)

(52) U.S. Cl.
CPC .............. *A61B 3/032* (2013.01); *A61B 3/005* (2013.01)

(58) Field of Classification Search
CPC ................................ A61B 3/032; A61B 3/005
USPC ......................................................... 351/222
See application file for complete search history.

(56) References Cited

U.S. PATENT DOCUMENTS

| | | | | |
|---|---|---|---|---|
| 8,346,518 B2 * | 1/2013 | Dupps, Jr. | ................ | G16B 5/00 606/5 |
| 2010/0026722 A1 * | 2/2010 | Kondo | ..................... | G09G 5/02 345/660 |
| 2016/0157712 A1 * | 6/2016 | Borden | .................. | A61B 3/005 351/222 |
| 2017/0052393 A1 | 2/2017 | Kweon | | |
| 2022/0326767 A1 * | 10/2022 | Altal | .................... | A61B 3/0285 |
| 2022/0383782 A1 * | 12/2022 | Lussier | .................. | G02B 30/10 |
| 2023/0341934 A1 | 10/2023 | Altal et al. | | |
| 2024/0225442 A1 | 7/2024 | Dave et al. | | |

OTHER PUBLICATIONS

International Search Report & Written Opinion mailed Dec. 27, 2024 for Intl. Appl. No. PCT/US2024/049015.

* cited by examiner

*Primary Examiner* — Mohammed A Hasan
(74) *Attorney, Agent, or Firm* — Husch Blackwell LLP; Bryan D. Stewart

(57) ABSTRACT

The present disclosure relates to a patient simulation system. The patient simulation includes a processor and a computer-readable medium storing instructions which, when executed by the processor, cause the processor to receive a selection of criteria for generating a patient simulation; generate a first view of the patient simulation corresponding to the selection of criteria to be viewed in two dimensions using a clinician display; generate a second view of the patient simulation corresponding to the selection of criteria to be viewed in three dimensions using a patient display; transmit the second view of the patient simulation to the patient display; and synchronize the first view to the second view by tracking a position and head orientation of the patient.

20 Claims, 17 Drawing Sheets

VISION CORRECTION SIMULATION SYSTEM AND METHODS OF USE

BACKGROUND

In an ophthalmologist's office, devices used to simulate vision correction, such as trial lenses and phoropters, are essential for accurately assessing and determining the appropriate prescription for patients. These tools allow patients to experience the potential improvement in their vision before committing to eyeglasses or contact lenses, ensuring a precise and comfortable fit. By providing a clear simulation of corrected vision, these devices help patients in making informed decisions about their vision care and improving overall visual health.

BRIEF SUMMARY OF THE DISCLOSURE

The present disclosure is directed generally to systems and methods for vision correction simulations and treatments including, by non-limiting example, the use of intraocular lenses (IOLs) and glasses. In certain embodiments, the vision correction simulation system is used to educate patients relating to how one or more vision correction treatments can be used to improve their vision. In certain embodiments, the vision correction simulation system is a synchronized system having a controller that generates one or more two-dimensional simulations that are translated for the patient to view on a patient display in three dimensions.

According to a first aspect of the present disclosure, a process for vision correction simulation comprises receiving a selection of criteria for generating a patient simulation; generating a first set of instructions, via a controller application, for displaying a first view of the patient simulation corresponding to the selection of criteria to be viewed in two dimensions using a first simulator application; generating a second set of instructions, via the controller application, for displaying a second view of the patient simulation corresponding to the selection of criteria to be viewed in three dimensions using a second simulator application; transmitting the first set of instructions to the first simulator application and the second set of instructions to the second simulator application; and synchronizing the first view to the second view by tracking a position and head orientation of a patient; wherein: the first set of instructions and the second set of instructions include manipulation criteria for manipulating one or more visual scenes by applying one or more filters or manipulating a mesh applied to the one or more visual scenes; the first view and the second view correspond to one or more visual scenes for displaying at least one of a visual effect, a vision correction treatment, and an ocular disorder; the visual effect comprises at least one of clear images, blurred images, double vision, lens cloudiness, glare, halos, and starbursts; the vision correction treatment comprises at least one of a monofocal IOL, monovision, an astigmatism correction, an extended depth of focus IOL, a symphony IOL, a cataract, a multifocal IOL, a lens filter, an anti-reflective coating, and an anti-glare feature; and the ocular disorder comprises at least one of myopia, hyperopia, astigmatism, presbyopia, and cataracts.

According to a second aspect of the first aspect or any other aspect, further comprising a patient display for displaying the second view.

According to a third aspect of the second aspect or any other aspect, further comprising collecting positional data and gyroscopic data using the patient display.

According to a fourth aspect of the third aspect or any other aspect, further comprising transmitting the positional data and the gyroscopic data to the controller application.

According to a fifth aspect of the second aspect or any other aspect, wherein the patient display is configured to display the second view to a patient.

According to a sixth aspect of the second aspect or any other aspect, wherein the patient display comprises at least one of an AR headset, a VR headset, and an XR headset.

According to a seventh aspect of the first aspect or any other aspect, wherein the blurred images comprise at least one of a far blur, an intermediate blur, and a near blur.

According to an eighth aspect of the first aspect or any other aspect, wherein the astigmatism correction includes at least one of a near astigmatism correction or a far astigmatism correction.

According to a ninth aspect of the first aspect or any other aspect, further comprising applying one or more ocular disorders to the first view and the second view.

According to a tenth aspect of the first aspect or any other aspect, wherein the first simulator application and the second simulator application are identical applications installed on a patient simulation system and a patient display.

According to an eleventh aspect of the present disclosure, a process for displaying one or more visual scenes comprises: receiving instructions for displaying the one or more visual scenes at a simulator application operating on a computing device from a controller application, wherein the instructions include one or more selections for the one or more visual scenes and manipulation criteria; loading the one or more visual scenes for display according to the one or more selections for the one or more visual scenes; manipulating the one or more visual scenes according to the manipulation criteria, wherein the manipulation criteria comprises at least one of applying one or more filters or manipulating a mesh applied to the one or more visual scenes; and displaying the one or more visual scenes in three dimensions; wherein: the one or more visual scenes comprise at least one of a visual effect, a vision correction treatment, and an ocular disorder; the visual effect comprises at least one of clear images, blurred images, double vision, lens cloudiness, glare, halos, and starbursts; the vision correction treatment comprises at least one of a monofocal IOL, monovision, an astigmatism correction, an extended depth of focus IOL, a cataract, a multifocal IOL, a lens filter, an anti-reflective coating, and an anti-glare feature; and the ocular disorder comprises at least one of myopia, hyperopia, astigmatism, presbyopia, and cataracts.

According to a twelfth aspect of the eleventh aspect or any other aspect, wherein the one or more visual scenes comprise at least one of a static scene or a dynamic scene.

According to a thirteenth aspect of the eleventh aspect or any other aspect, further comprising adjusting a degree of the one or more visual effects.

According to a fourteenth aspect of the eleventh aspect or any other aspect, further comprising adjusting a degree of the one or more ocular disorders.

According to a fifteenth aspect of the eleventh aspect or any other aspect, further comprising adjusting a degree of the one or more vision correction treatments.

According to a sixteenth aspect of the eleventh aspect or any other aspect, further comprising: transmitting gyroscopic data and positional data; and receiving subsequent instructions based on the gyroscopic and positional data.

According to a seventeenth aspect of the present disclosure, a process for vision correction simulation comprises: receiving a selection of criteria for generating a patient simulation; generating a first set of instructions, via a controller application, for displaying a first view of the patient simulation corresponding to the selection of criteria to be viewed in two dimensions using a first simulator application; generating a second set of instructions, via the controller application, for displaying a second view of the patient simulation corresponding to the selection of criteria to be viewed in three dimensions using a second simulator application; transmitting the first set of instructions to the first simulator application and the second set of instructions to the second simulator application; and synchronizing the first view to the second view by tracking a position and head orientation of a patient; wherein: the first set of instructions and the second set of instructions include manipulation criteria for manipulating one or more visual scenes by applying one or more filters or manipulating a mesh applied to the one or more visual scenes; and the first view and the second view correspond to one or more visual scenes for displaying at least one of a visual effect, a vision correction treatment, and an ocular disorder.

According to an eighteenth aspect of the seventeenth aspect or any other aspect, wherein the visual effect further comprises at least one of clear images, blurred images, double vision, lens cloudiness, glare, halos, and starbursts.

According to a nineteenth aspect of the seventeenth aspect or any other aspect, wherein the vision correction treatment comprises at least one of a monofocal IOL, monovision, an astigmatism correction, an extended depth of focus IOL, a cataract, a multifocal IOL, a lens filter, an anti-reflective coating, and an anti-glare feature.

According to a twentieth aspect of the seventeenth aspect or any other aspect, wherein the ocular disorder comprises at least one of myopia, hyperopia, astigmatism, presbyopia, and cataracts.

According to a twenty-first aspect, a patient simulation system comprises: a processor; and a computer-readable medium storing instructions which, when executed by the processor, cause the processor to: receive a selection of criteria for generating a patient simulation; generate a first view of the patient simulation corresponding to the selection of criteria to be viewed in two dimensions using a clinician display; generate instructions corresponding to a second view of the patient simulation corresponding to the selection of criteria to be viewed in three dimensions using a patient display; transmit the instructions to the patient display; and synchronize the first view to the second view by tracking a position and head orientation of a patient, wherein: wherein the first view and the second view correspond to one or more visual scenes for displaying one or more visual effects, and the one or more visual effects comprise at least one of clear images, blurred images, double vision, lens cloudiness, glare, halos, and starbursts.

According to a twenty-second aspect of the twenty-first aspect or any other aspect, further comprising the patient display.

According to a twenty-third aspect of the twenty-second aspect or any other aspect, wherein the patient display is configured to display the second view to a patient.

According to a twenty-fourth aspect of the twenty-second aspect or any other aspect, wherein the patient display comprises at least one of an AR headset, a VR headset, and an XR headset.

According to a twenty-fifth aspect of the twenty-first aspect or any other aspect, wherein the computer-readable medium stores the one or more visual scenes.

According to a twenty-sixth aspect of the twenty-first aspect or any other aspect, wherein the blurred images comprise at least one of a far blur, an intermediate blur, and a near blur.

According to a twenty-seventh aspect of the twenty-first aspect or any other aspect, wherein a degree of the one or more visual effects is adjustable.

According to a twenty-eighth aspect of the twenty-first aspect or any other aspect, wherein the computer-readable medium stores instructions which, when executed by the processor, further cause the processor to apply one or more vision correction treatments to the first view and the second view.

According to a twenty-ninth aspect of the twenty-eighth aspect or any other aspect, wherein the one or more vision correction treatments comprise at least one of a monofocal IOL, monovision, an astigmatism correction, an extended depth of focus IOL, an extended depth of focus and multifocal IOL, a cataract, a multifocal IOL, a lens filter, an anti-reflective coating, and an anti-glare feature.

According to a thirtieth aspect of the twenty-ninth aspect or any other aspect, wherein the astigmatism correction includes at least one of a near astigmatism correction or a far astigmatism correction.

According to a thirty-first aspect of the twenty-first aspect or any other aspect, wherein the computer-readable medium stores instructions which, when executed by the processor, further cause the processor to apply one or more ocular disorders to the first view and the second view.

According to a thirty-second aspect of the thirty-first aspect or any other aspect, wherein the one or more ocular disorders include emmetropia, myopia, hyperopia, astigmatism, presbyopia, and cataracts.

According to a thirty-third aspect of the thirty-first aspect or any other aspect, wherein a degree of the one or more ocular disorders is adjustable.

According to a thirty-fourth aspect of the present disclosure, a method for displaying one or more visual scenes to a patient comprises: receiving instructions for displaying the one or more visual scenes, wherein the instructions include one or more selections for the one or more visual scenes and manipulation criteria; loading the one or more visual scenes for display according to the one or more selections for the one or more visual scenes; manipulating the one or more visual scenes according to the manipulation criteria; and displaying the one or more visual scenes in three dimensions to the patient; wherein: the one or more visual effects include at least one of clear images, blurred images, double vision, lens cloudiness, glare, halos, and starbursts; and the blurred images comprise at least one of a far blur, an intermediate blur, and a near blur.

According to a thirty-fifth aspect of the thirty-fourth aspect or any other aspect, further comprising: receiving one or more subsequent sets of instructions comprising additional manipulation criteria; and manipulating the one or more scenes in real time according to the additional manipulation criteria.

According to a thirty-sixth aspect of the thirty-fourth h aspect or any other aspect, wherein the one or more visual scenes comprise at least one of a static scene or a dynamic scene.

According to a thirty-seventh aspect of the thirty-fourth aspect or any other aspect, wherein the manipulation criteria comprises one or more visual effects.

According to a thirty-eighth aspect of the thirty-seventh aspect or any other aspect, further comprising adjusting a degree of the one or more visual effects.

According to a thirty-ninth aspect of the thirty-fourth aspect or any other aspect, wherein the manipulation criteria comprises one or more vision correction treatments.

According to a fortieth aspect of the thirty-ninth aspect or any other aspect, wherein the one or more vision correction treatments comprise at least one of a monofocal IOL, monovision, an astigmatism correction, an extended depth of focus IOL, an extended depth of focus and multifocal IOL, a cataract, a multifocal IOL, a lens filter, an anti-reflective coating, and an anti-glare feature.

According to a forty-first aspect of the thirty-forth aspect or any other aspect, wherein the manipulation criteria comprises one or more ocular disorders.

According to a forty-second aspect of the forty-first aspect or any other aspect, wherein the one or more ocular disorders comprise at least one of emmetropia, myopia, hyperopia, astigmatism, presbyopia, and cataracts.

According to a forty-third aspect of the forty-first aspect or any other aspect, further comprising adjusting a degree of the one or more ocular disorders.

According to a forty-fourth aspect of the present disclosure, a method of determining a vision correction plan for a patient comprises: receiving a selection of criteria for generating a patient simulation; displaying the patient simulation to the patient, wherein the patient simulation comprises: one or more visual effects comprising at least one of clear images, blurred images, double vision, lens cloudiness, glare, halos, and starbursts; one or more vision correction treatments corresponding to the one or more visual effects; receiving feedback from the patient corresponding to the patient simulation; determining whether the one or more vision correction treatments is effective in treating the one or more visual effects; and generating the vision correction plan when the one or more vision correction treatments is effective in treating the one or more visual effects.

According to a forty-fifth aspect of the forty-fourth aspect or any other aspect, wherein the patient simulation further comprises one or more ocular disorders.

According to a forty-sixth aspect of the forty-fifth aspect or any other aspect, wherein the one or more ocular disorders comprise at least one of emmetropia, myopia, hyperopia, astigmatism, presbyopia, and cataracts.

According to a forty-seventh aspect of the forty-fourth aspect or any other aspect, further comprising adjusting a degree of the one or more visual effects.

According to a forty-eighth aspect of the forty-fourth aspect or any other aspect, wherein the one or more vision correction treatments comprise at least one of a monofocal IOL, monovision, an astigmatism correction, an extended depth of focus IOL, an extended depth of focus and multi-focal IOL, a cataract, a multifocal IOL, a lens filter, an anti-reflective coating, and an anti-glare feature.

According to a forty-ninth aspect of the present disclosure, a method of determining a vision correction plan for a patient comprises: receiving a selection of criteria for generating a patient simulation; displaying the patient simulation to the patient, wherein the patient simulation comprises: one or more visual effects comprising at least one of clear images, blurred images, double vision, lens cloudiness, glare, halos, and starbursts; one or more vision correction treatments corresponding to the one or more visual effects; and one or more ocular disorders corresponding to a condition of a patient including at least one of emmetropia, myopia, hyperopia, astigmatism, presbyopia, and cataracts; receiving feedback from the patient corresponding to the patient simulation; determining an appropriate vision correction plan for treating the one or more visual effects; and generating the vision correction plan when the one or more vision correction treatments is effective in treating the one or more visual effects.

According to a fiftieth aspect of the forty-ninth aspect or any other aspect, further comprising adjusting a degree of the one or more visual effects.

According to a fifty-first aspect of the forty-ninth aspect or any other aspect, further comprising adjusting a degree of the one or more ocular disorders.

According to a fifty-second aspect of the forty-ninth aspect or any other aspect, further comprising adjusting a degree of the one or more vision correction treatments.

According to a fifty-third aspect of the forty-ninth aspect or any other aspect, wherein the one or more vision correction treatments comprise at least one of a monofocal IOL, monovision, an astigmatism correction, an extended depth of focus IOL, an extended depth of focus and multifocal IOL, a cataract, a multifocal IOL, a lens filter, an anti-reflective coating, and an anti-glare feature.

BRIEF DESCRIPTION OF THE DRAWINGS

The foregoing Summary and the following Detailed Description will be better understood when read in conjunction with the appended drawings. In the drawings.

DETAILED DESCRIPTION

The following detailed description of the invention references specific embodiments in which the certain embodiments of the present disclosure can be practiced. The embodiments are intended to describe aspects of the present disclosure in sufficient detail to enable those skilled in the art to practice the invention. Other embodiments can be utilized, and changes can be made without departing from the scope of the present invention. It will be appreciated that some or all the various features and structures described and shown with respect to each of the specific embodiments referenced herein may be combined to form additional or alternative embodiments having such combinations and that such combinations are within the scope of the present invention.

The present disclosure generally relates to systems and methods for simulating the effects of one or more vision correction options and ocular conditions to a patient for the purposes of educating one or more patients.

Ophthalmologists, optometrists, and opticians educate patients about one or more vision correction options that are available to them prior to selecting one or more options for treating the patient. It is desirable to educate patients on vision correction options before selecting a course of treatment to ensure informed decision-making aligned with a patient's specific eye health needs and preferences. Understanding the available treatments, their benefits, potential risks, and expected outcomes empowers patients to participate actively in their eye care, fostering trust and enhancing treatment effectiveness.

Thus, ophthalmologists, optometrists and opticians use devices to simulate vision correction, such as trial lenses and phoropters, to help assess and determine the appropriate prescription for patients and teach the patients about their prescription. These tools allow patients to experience the potential improvement in their vision before committing to eyeglasses or contact lenses, ensuring a precise and comfortable fit. By providing a clear simulation of corrected vision, these devices help patients in making informed decisions about their decision to update their glasses or contacts to help improve their vision. By allowing them to have an idea of what their vision could be with the new prescription allows them to make an informed decision as to their expected vision before purchasing expensive lenses.

It is desirable to show patients what certain lens options would look like in different environments and lighting. Further, it is desirable to show patients what these options would look like in typical environments (e.g., what the patient may see while sitting in an office or while driving an automobile). Providing a means to show patients various vision correction options in an immersive three-dimensional environment would provide a more complete understanding of how these options perform in the typical environments.

Figure 1:
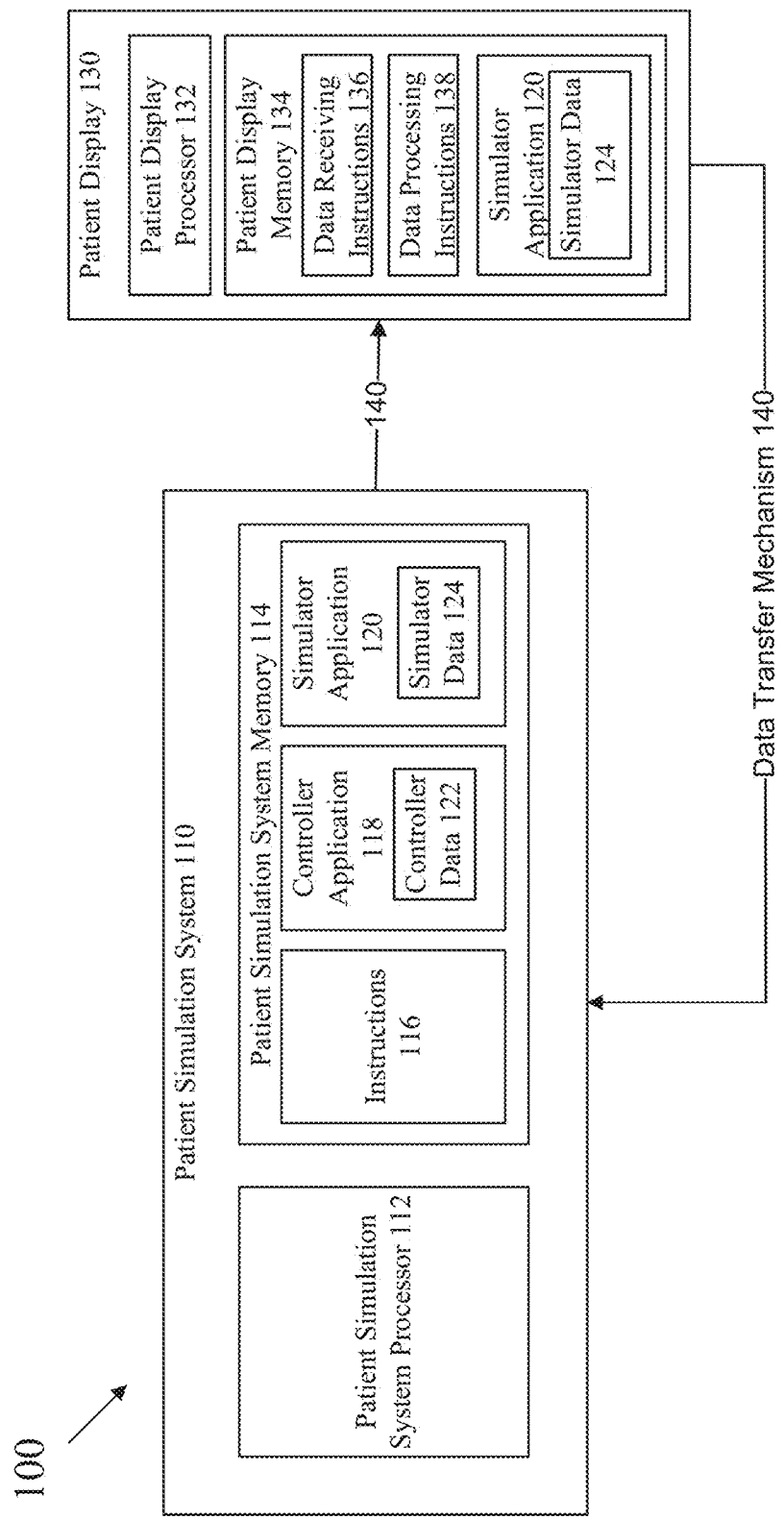
FIG. 1 is a schematic diagram showing a patient simulation system and an external patient display communicating via a data transfer mechanism, in accordance with one or more embodiments of the present disclosure.

FIG. 1 is a schematic diagram showing a system 100 including a patient simulation system 110 and a patient display 130 communicating via a data transfer mechanism 140, in accordance with one or more embodiments of the present disclosure.

In at least one embodiment, the patient simulation system 110 includes a patient simulation system processor 112 and a patient simulation system memory 114. In certain embodiments, the patient simulation system memory 114 is a computer-readable medium storing instructions which, when executed by the processor, cause the processor to perform one or more operations. In certain embodiments, the processor may perform one or more operations as illustrated and described in FIGS. 2-15, alone or in conjunction with processor 132 discussed below.

Systems and software, e.g., implemented on a non-transitory computer-readable medium (e.g., the patient simulation system memory 114 and/or patient display memory 134) for performing the methods discussed herein are within the scope of embodiments of the present disclosure and may utilize a special purpose or general-purpose computing system including computer hardware, such as, for example, one or more processors (e.g., the patient simulation system processor 112) and system memory (e.g., the patient simulation system memory 114).

Embodiments within the scope of the present disclosure also include physical and other computer-readable media for carrying or storing computer-executable instructions 116 and/or data structures, including applications, tables, data, libraries, or other modules used to execute functions or direct selection or execution of other modules. Such computer-readable media can be any available media that can be accessed by a general purpose or special purpose computer system. Computer-readable media that store computer-executable instructions (or software instructions) are physical storage media. Computer-readable media that carry computer-executable instructions are transmission media. Thus, by way of example, and not limitation, embodiments of the present disclosure can include at least two distinctly different kinds of computer-readable media, namely physical storage media or transmission media. Combinations of physical storage media and transmission media should also be included within the scope of computer-readable media.

Both physical storage media and transmission media may be used temporarily to store or carry software instructions in the form of computer readable program code that allows performance of embodiments of the present disclosure. Physical storage media may further be used to persistently or permanently store such software instructions. Examples of physical storage media include physical memory (e.g., RAM, ROM, EPROM, EEPROM, etc.), optical disk storage (e.g., CD, DVD, HDDVD, Blu-ray, etc.), storage devices (e.g., magnetic disk storage, tape storage, diskette, etc.), flash or other solid-state storage or memory, or any other non-transmission medium which can be used to store program code in the form of computer-executable instructions or data structures and which can be accessed by a general purpose or special purpose computer, whether such program code is stored as or in software, hardware, firmware, or combinations thereof.

A data transfer mechanism 140 may generally be defined as one or more data links that enable the transport of electronic data between computer systems and/or modules, engines, and/or other electronic devices. When information is transferred or provided over a communication network or another communications connection (either hardwired, wireless, or a combination of hardwired or wireless such as one or more of a Bluetooth connection, a Wi-Fi connection, a LAN connection, or another form of wired connection) to a computing device, the computing device properly views the connection as a transmission medium. Transmission media can include a communication network and/or data links, carrier waves, wireless signals, and the like, which can be used to carry desired program or template code means or instructions in the form of computer-executable instructions or data structures and which can be accessed by a general purpose or special purpose computer. As illustrated and described in FIG. 1, the data transfer mechanism 140 enables transport of electronic data between the patient simulation system 110 and the patient display 130 which are illustrated and described in further detail below.

Further, upon reaching various computer system components, program code in the form of computer-executable instructions or data structures can be transferred automatically or manually from transmission media to physical storage media (or vice versa). For example, computer-executable instructions or data structures received over a network or data link can be buffered in memory (e.g., RAM) within a network interface module (NIC), and then eventually transferred to computer system RAM and/or to less volatile physical storage media at a computer system. Thus, physical storage media can be included in computer system components that also (or even primarily) utilize transmission media.

In certain embodiments, the patient simulation system memory includes a controller application 118. In some embodiments, the controller application 118 is operated by a clinical care provider (e.g., an ophthalmologists, optometrists, or opticians) to generate a first view of a patient simulation to be viewed by the clinical care provider in two dimensions.

In various embodiments, the simulator application 120 receives controller data 122 from the controller application 118 to generate a second view of the patient simulation to be viewed by the patient in three dimensions. As discussed herein, the controller data 122 may include any suitable instructions or data. In at least one embodiment, the controller data 122 includes instructions for the simulator application to load a particular scene (e.g., access a base 3D scene from memory and display the base 3D scene). In some embodiments, the controller data 122 includes instructions for modifying a view of the particular scene, based on, for example, patient data (e.g., current vision state of a patient, such as astigmatism), which may include instructions for modifying one or more cameras, filters, or meshes to distort the particular scene. According to particular embodiments, the controller data 122 includes data for modifying a view of the particular scene to represent one or more vision correction options as discussed herein (which might include instructions for modifying or applying a camera, a filter, a mesh, etc.). As will be understood from discussions herein, the simulator application 120 may continuously receive controller data 140 from the controller application so the 3D view displayed to a patient substantially mirrors changes to the patient view as shown in 2D on the patient simulation system 110. In certain embodiments, and as shown in FIG. 1, the simulator application 120 may be stored within the patient simulation system memory 114 and the patient display memory 134 to allow a patient simulation to be viewed on the patient simulation system 110 and the patient display 130. Furthermore, in certain embodiments, the simulator application 120 may be stored within the patient simulation system memory 114 as a first simulator application and the patient display memory 134 as a second simulator application to allow for simultaneous transfer of data from the controller application 118 to the first simulator application and the second simulator application.

In certain embodiments, the second view of the patient simulation is viewed by the patient using a patient display 130, which is illustrated and described in further detail below.

In certain embodiments, the controller application 118 is configured to control the simulator application 120 by receiving a selection of criteria from a user (e.g., the clinical care provider) and providing instructions to the simulator application to generate the second view of the patient simulation that corresponds to the first view generated by the controller application 118. The controller application 118 is configured to receive a selection of criteria relating to one or more visual effects 410 (not shown), vision correction treatments 430 (not shown) and one or more ocular disorders 450 (not shown), which are illustrated and described in further detail with respect to FIGS. 6-15. In certain embodiments, the controller application 118 generates the first view in two dimensions, provides instructions for the simulator application 120 to generate the second view (which includes the same scene as the first view, but in three dimensions) to be displayed on the patient display 130, and synchronizes the first view to the second view by tracking a position and a head orientation of the patient.

Synchronizing the first view and the second view between the controller application 118 and the simulator application 120 generally involves establishing a connection or integration that allows data and actions from one application to be mirrored or coordinated with those in another. This synchronization ensures that patients see consistent information and can seamlessly interact across different platforms or interfaces, enhancing usability and productivity in software environments. Further, this ensures that any changes made by the clinical care provider in the controller application 118 are synchronized to the simulator application 120 in real time. This enables the clinical care provider to see the same patient simulation in two dimensions that the patient is viewing in three dimensions while also seeing any changes made to the patient's view in real time. These changes made to the patient's view can be made based on changes to the patient's head orientation and position or changes made by the clinical care provider at the controller application 118. Thus, the patient simulation system 110 synchronizes the patient simulation between the clinical care provider's view at the controller application 118 and the patient's view at the patient display 130 by exchanging controller data 122 (e.g., the selection of criteria for the patient simulation from the clinical care provider) and simulator data 124 (e.g., the patient's head orientation and position) between the controller application 118 and the simulator application 120.

In certain embodiments, the changes made to the patient's view based on changes to the patient's head orientation and position changes are completed as follows. One or more sensors in the patient display 130 (e.g., a gyroscope or accelerometer) measure the orientation and movement of the patient display 130 in real time as the patient display 130 is attached to the head of a patient. The patient display 130 stores this data as simulator data 124 to track the precise position and orientation of the patient's head in a three-dimensional space. In certain embodiments, this includes six degrees of freedom (i.e., patient movement along three axes (x, y, z) and rotation around those axes (pitch, yaw, roll). As the patient moves their head, the patient display 130 updates the virtual scene displayed in the headset to match the new perspective. This can be done by rendering the scene from the new viewpoint calculated based on the tracked head position and orientation. Furthermore, in certain embodiments, the patient display 130 may include other controllers and sensors beyond that of a headset, such as hand controllers or other input devices.

Furthermore, it is desirable to minimize latency (the delay between head movement and a scene update) to improve immersion and prevent motion sickness. A process by which data is smoothly sent between the controller application 118 and the simulator application 120 to minimize latency is illustrated and described in further detail below with respect to FIG. 17.

In at least one embodiment, the controller application 118 includes controller data 122 and the simulator application 120 includes simulator data 124. In certain embodiments, the controller data 122 and the simulator data 124 include pre-built patient simulations that are synchronized together to include the same scene (i.e., the controller data 122 includes a two-dimensional scene and the simulator data 124 includes a three-dimensional rendering of the same scene stored in the controller data 122).

In certain embodiments, the controller application 118 transmits controller data 122, including data arrays associated with visual effects, to the simulator application 120. This data may contain adjustable values for one or more object meshes and camera filters that form each patient simulation. In a non-limiting example, a patient simulation can be created by taking real-world models and objects in three dimensions and splicing them together to make a three-dimensional scene of a common setting (e.g., a kitchen within a home). In certain embodiments, the patient simulation can be static or dynamic. Examples of static and dynamic scenes are illustrated and described in further detail with respect to FIGS. 7-15.

In certain embodiments, the patient simulation includes a camera (i.e., a viewing point from the patient within the virtual reality display) built within the patient simulation to track the patient's gaze, head orientation, and head position. This tracking can include one or more of the use of headset sensors (e.g., accelerometers, gyroscopes, or magnetometers for continuously monitoring the orientation and position of the headset in three-dimensional space), gaze tracking (e.g., the use of eye-tracking sensors), head tracking (e.g., a process of continuously updating the position and orientation of the user's head relative to a VR environment), and real-time rendering within a VR app's scenes to dynamically adjust a viewpoint of a user based on the user's head movements and gaze direction.

In certain embodiments, the camera follows the patient's real-time position by tracking the patient's gaze, head orientation, and head position as discussed above. It is desirable to maximize the immersion of the patient within the one or more patient simulations to provide an understanding of how one or more ocular treatments may impact the patient. The camera locations may view objects at varying distances with varying effects, which are illustrated and described in further detail with respect to FIGS. 7-15.

The system 100 includes a patient display 130 for displaying one or more patient simulations generated by the patient simulation system 110. The patient display 130 can include any means for viewing the patient simulation as recognizable by one of ordinary skill in the art. In certain embodiments, the patient display 130 is an augmented reality (AR) headset or glasses, a virtual reality (VR) headset or glasses, or an extended reality (XR) headset or glasses.

An AR headset overlays digital information, such as images, text, or animations, onto the real-world environment. This technology enhances the user's perception of reality by blending virtual elements with the physical world. While typically viewed through a device like a smartphone or AR glasses, augmented reality can be viewed through any other suitable means as recognizable by one of ordinary skill in the art.

In certain embodiments, a patient may view the real world through an AR headset with a proposed treatment from a clinician. In a non-limiting example, the patient may view the real world through the AR lens, observe their view as having one or more clinical conditions (e.g., lens cataracts, astigmatism, or blurriness) and have an AR display that corrects the one or more clinical conditions.

A VR headset creates a completely immersive digital environment that simulates physical presence in a computer-generated world. Users typically experience VR through head-mounted displays (HMDs), which block out the real world and immerse them in a virtual environment.

A XR headset encompasses AR, VR, and other immersive technologies. It refers to the spectrum of environments that blend the physical world with digital elements, ranging from purely virtual (VR) to partially augmented (AR). XR serves as an umbrella term encompassing both AR and VR, highlighting their shared goal of blending digital and physical realities to varying degrees of immersion and interaction.

Although references are made to AR, VR, and XR displays, the patient display 130 is herein defined to include any combination of AR, VR, and XR display technology and is not intended to be limited to any single technology or combination of technologies. Furthermore, the patient display 130 can include any form of two-dimensional display or flat panel display.

Furthermore, the patient display 130 includes a patient display processor 132 and a patient display memory 134. The patient display memory 134 stores instructions which, when executed by the patient display processor 132, causes the patient display processor 132 to perform one or more of the functionalities of the patient display 130 described herein. Furthermore, the patient display memory 134 includes data receiving instructions 136 and data processing instructions 138. The data receiving instructions 136 and the data processing instructions 138 are configured to aid in the synchronization of the patient display 130 with the patient simulation system 110. In certain embodiments, the patient display processor 132 receives data from the patient simulation system 110, including controller data 122, and adjusts a scene displayed on the patient display 130 to match one or more parameters determined using the controller application 118.

Figure 2:
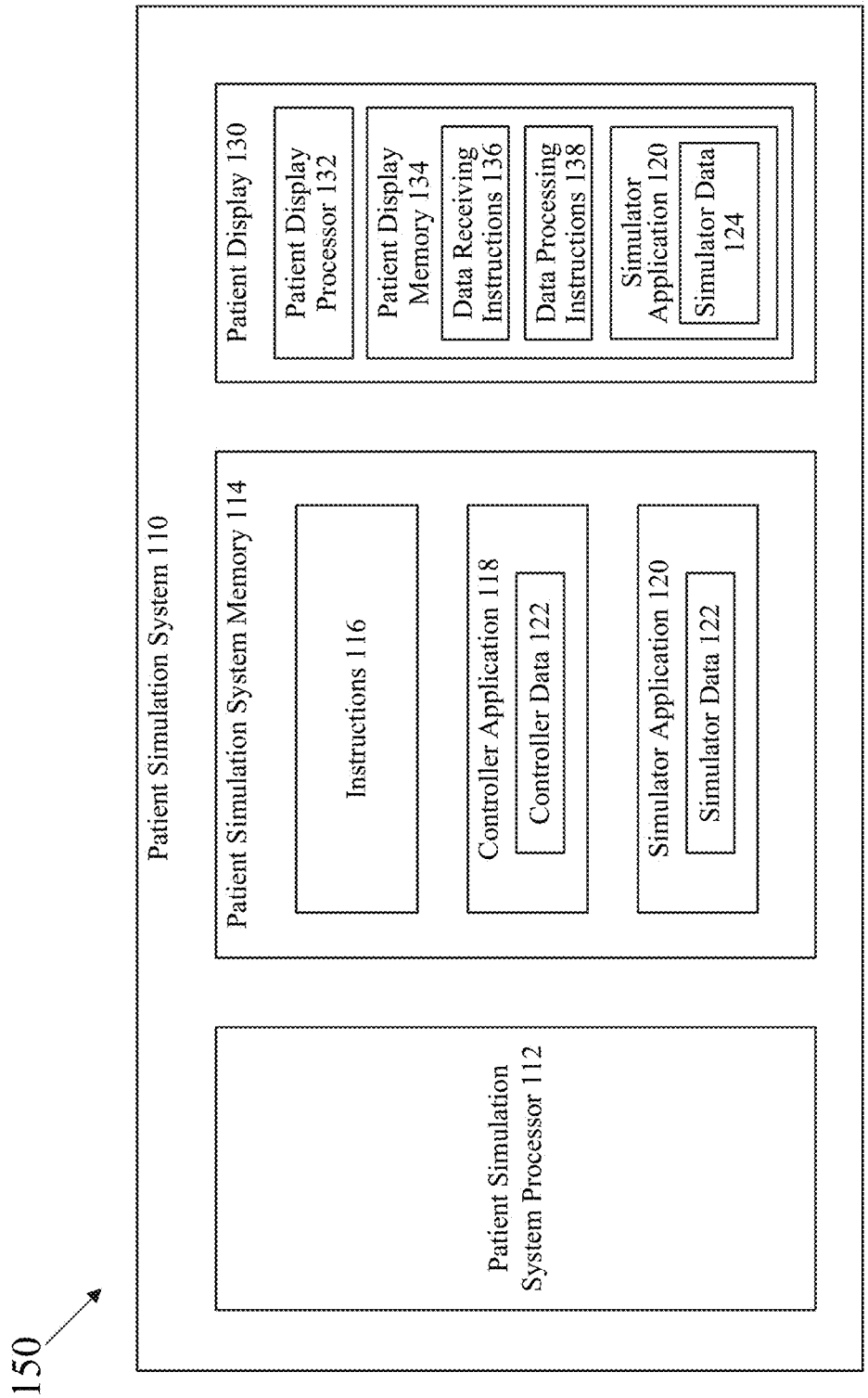
FIG. 2 is a schematic diagram showing a patient simulation system and an internal patient display, in accordance with one or more embodiments of the present disclosure.

FIG. 2 is a schematic diagram showing a patient simulation system and an internal patient display, in accordance with one or more embodiments of the present disclosure. FIG. 2 illustrates another example embodiment of the system 150 including the patient simulation system. In certain embodiments, the patient simulation system includes the patient simulation processor 112 and patient simulation system memory as illustrated and described above in further detail with respect to FIG. 1. Further, the patient simulation system 110 may include the patient display 130 as part of an internal component of the simulations system 110. In certain embodiments, the patient display 130 may include a monitor for displaying a three-dimensional rendering of a patient simulation. Furthermore, in certain embodiments, one or more components of the patient display 130, including the patient display processor 132, the patient display memory 134, and the components of the patient display memory (e.g., the data receiving instructions 136 the data processing instructions 138, and the simulator application 120 may be included as a component of the patient simulation system 110.

Figure 3:
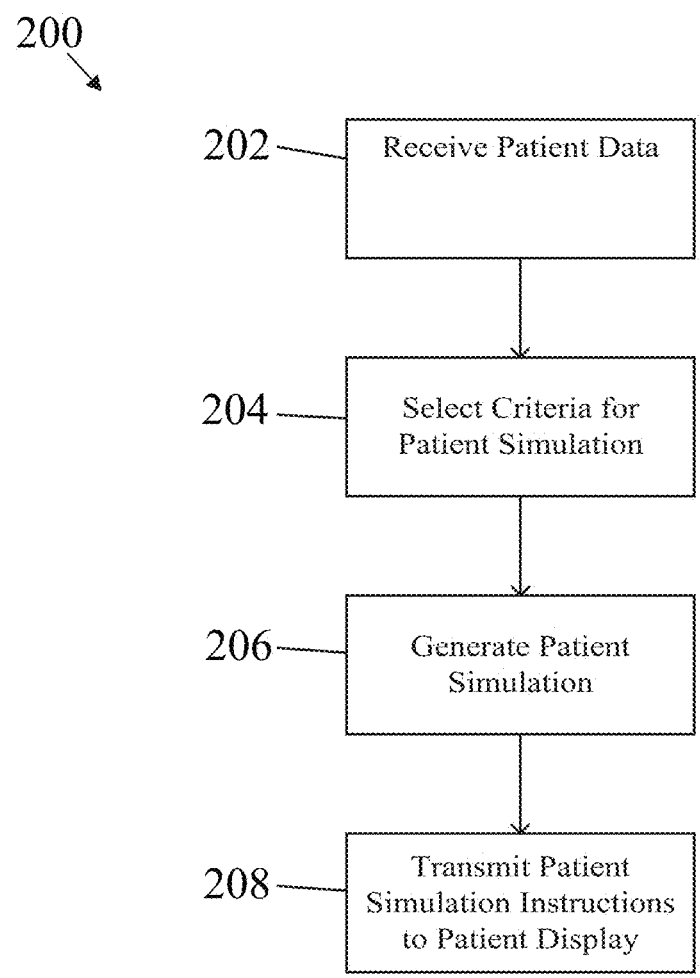
FIG. 3 is a method flow diagram of generating a patient simulation based on patient data and displaying the patient simulation to a patient, according to one embodiment of the present disclosure.

FIG. 3 is a method flow diagram of a method 200 for generating a patient simulation based on patient data and displaying the patient simulation to a patient, according to one embodiment of the present disclosure.

In certain embodiments, the method 200 may include a step 202 of receiving patient data. Patient data can be received from any memory storage system that stores patient data as recognizable by one of ordinary skill in the art. In certain embodiments, this can include at least one of an electronic health record (EHR) system, a picture archiving and communication (PACS) system, a hospital information system (HIS), and a laboratory information management system (LIMS). Furthermore, patient data can also be received from a patient intake form or another form of computing device such as a tablet, computer, cellular phone, or the like.

Furthermore, in certain embodiments, the patient data can be received and processed automatically by the system 100 to generate a personalized patient simulation that is unique to an individual based on their patient data. In a non-limiting example, the system may analyze an individual's patient data to determine the individual is near-sighted and accordingly adjust the patient simulation to include a mesh filter that blurs objects that are positioned far away from the individual's viewpoint. In certain embodiments, this automatic process can be done to initialize the patient simulation, and one or more vision correction treatments 430 (not shown) can then be introduced to correct the initial visual effect 410 (not shown).

The method 200 includes a step 204 of selecting one or more criteria for the patient simulation. In certain embodiments, step 204 is performed by the clinical care provider using the controller application 118. This can include, by non-limiting example, criteria for a specific scene or various treatment criteria such as visual effects 410 (not shown), vision correction treatments 430 (not shown), and ocular disorders 450 (not shown), which are illustrated and described in further detail with respect to FIG. 6.

In an alternative embodiment, the system 100 may automatically determine criteria for the patient simulation based on, by non-limiting example, the patient data received in step 202.

The method 200 includes a step 206 of generating the patient simulation. As illustrated and described above with respect to FIG. 1, the patient simulation is generated by creating a scene with real world models and objects that are spliced together to create a realistic scene of everyday life. The scene may include a specific viewpoint (or camera) for viewing one or more objects from a strategic location (e.g., a near, intermediate, or far distance). Once a camera is in place and the 3D objects are positioned within the scene using unique mesh covers, a unique filter can be overlayed on top of the scene to include the visual effects 410 (not shown), vision correction treatments 430 (not shown), and ocular disorders 450 (not shown), which are illustrated and described in further detail with respect to FIG. 6. In certain embodiments, the visual effects 410 (not shown), vision correction treatments 430 (not shown), and ocular disorders 450 (not shown) are generated based on patient data that correlates to one or more patient conditions that are simulated using the mesh covers to create effects, treatments, and disorders that uniquely relate to a patient's condition.

The method 200 includes a step 208 of transmitting the patient simulation instructions to the patient display 130. Once the patient simulation is generated by the controller application 118 in two dimensions, it is transmitted to the simulator application 120 to be viewed by the patient in three dimensions using the patient display 130 as illustrated and described above with reference to FIG. 1.

Figure 4:
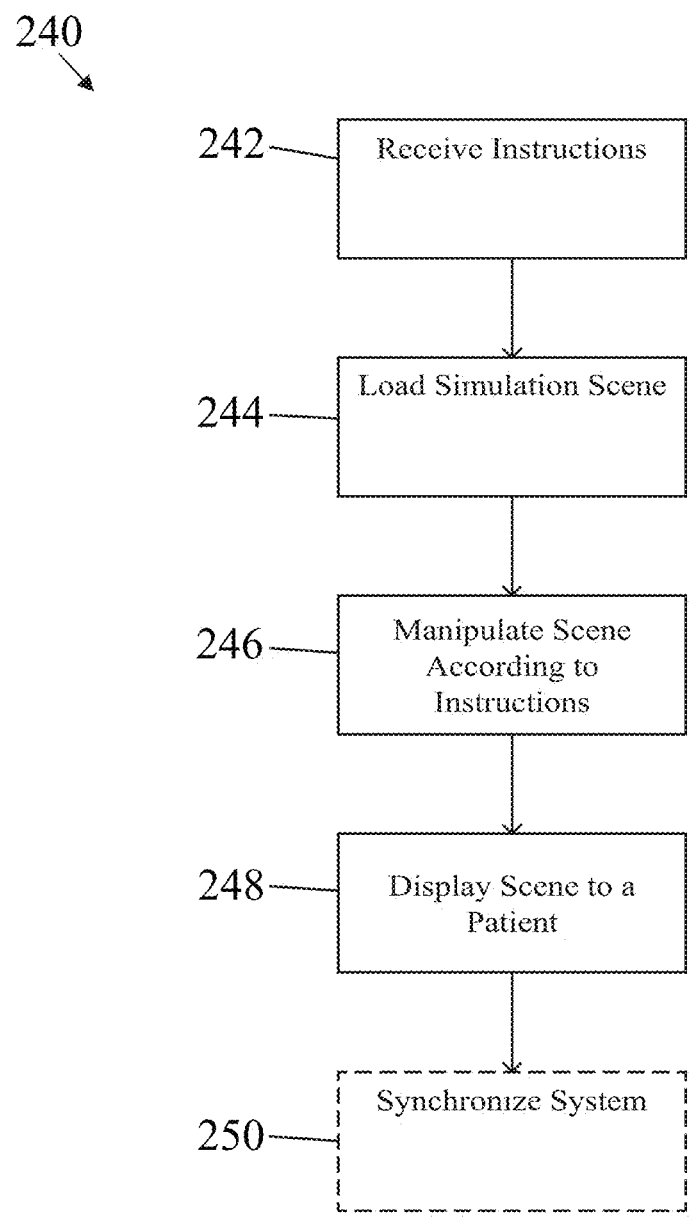
FIG. 4 is a method flow chart of a method 240 for displaying a scene to a patient using the patient display device 130, according to one embodiment of the present disclosure.
Figure 5:
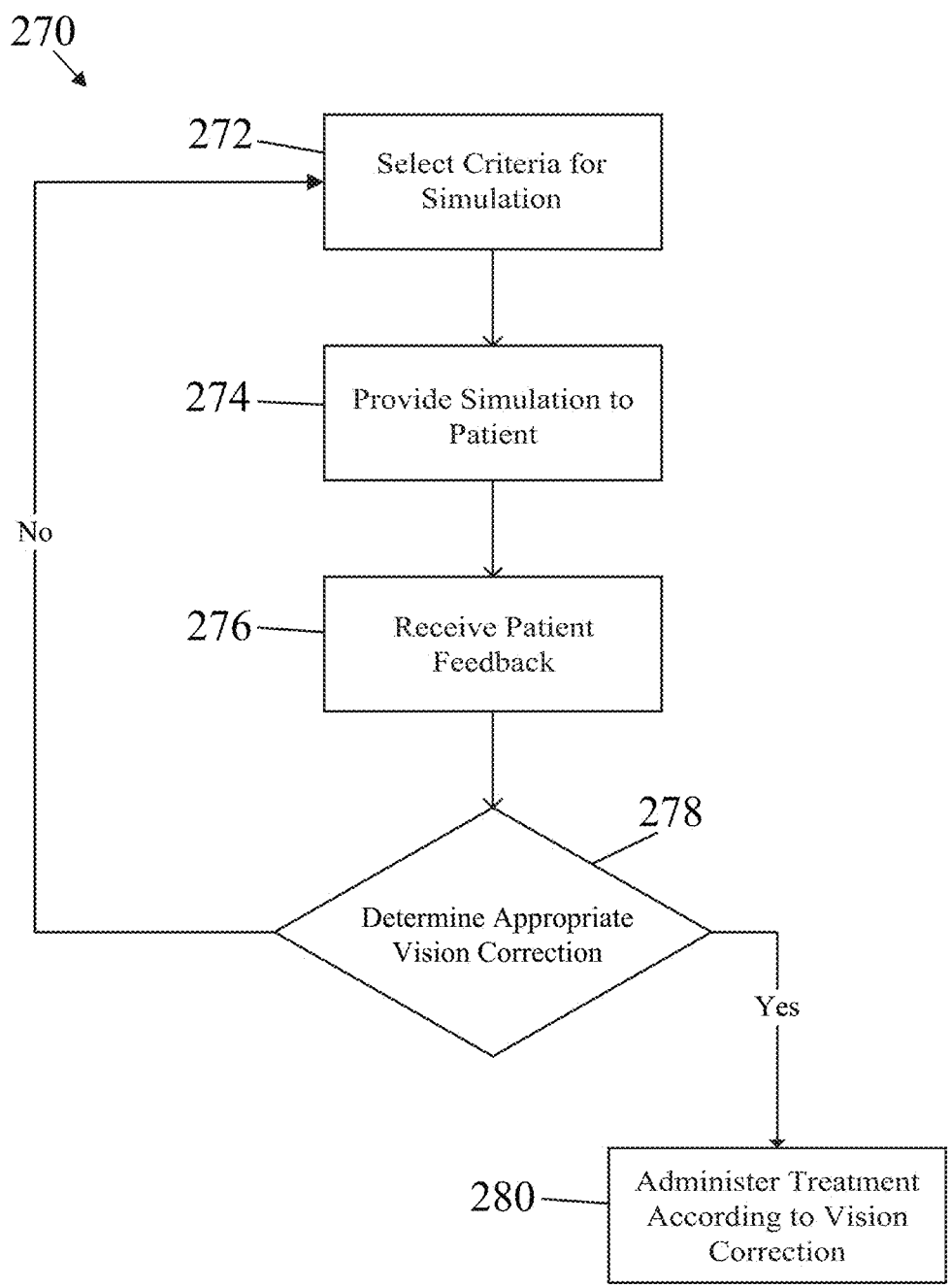
FIG. 5 is a method flow chart of a method 270 for determining an effective vision correction and administering a treatment to a patient according to the vision correction, according to one embodiment of the present disclosure.

FIG. 4 is a method flow chart of a method 240 for displaying a scene to a patient using the patient display 130.

The method 240 includes a step 242 of receiving patient data. The patient data can be received from the patient simulation system 110 or any other system illustrated and described above with reference to FIG. 2. Various types of data that can be received by the system 100. In various embodiments, the data can include preoperative metrics and patient biometry. The preoperative metrics may include, by non-limiting example, ocular health metrics such as an intraocular pressure, a corneal thickness, information pertaining to a gonioscopy, retinal thickness, visual field, and metrics pertaining to a pupil's response to light. Furthermore, the preoperative metrics may include, by non-limiting example, a degree of refractive error measuring the extent to which an individual's eyes do not properly focus light onto the retina, affecting vision clarity. The degree of refractive error quantifies nearsightedness (myopia), farsightedness (hyperopia), or astigmatism, with higher numerical values indicating greater severity of the refractive error. Further yet, the patient biometry may include, by non-limiting example, an axial length, keratometry, an anterior chamber depth, and other measurements.

The method 240 includes a step 244 of loading a simulation scene. In certain embodiments, the simulation scene is loaded from a local storage at the patient display memory 134. In certain embodiments, the simulation scene is loaded onto the patient display 130 using the simulator application 120. The simulator application 120 receives data relating to the simulation scene from the controller application 118 as illustrated and described in FIG. 1.

The method 240 includes a step 246 of manipulating the simulation scene according to instructions from the simulator application 120 or the controller application 118. The instructions can include one or more manipulation criteria for manipulating the patient simulation to include a visual effect, a vision correction treatment, or an ocular disorder, which is illustrated and described in further detail with respect to FIG. 6. In certain embodiments, the manipulation of the scene is done by receiving one or more inputs from a clinician using the controller application 118. The one or more inputs may relate to the visual effects 410 (not shown), vision correction treatments 430 (not shown), and ocular disorders 450 (not shown), which are illustrated and described in further detail with respect to FIG. 6. The one or more inputs can be transmitted from the controller application 118 to the simulator application 120 to implement the one or more inputs by manipulating the scene that is shown to the patient in three dimensions at the patient display 130.

The method 240 includes a step 248 of displaying a scene to the patient using the patient display 130. Processes for displaying the scene to the patient using the patient display 130 is illustrated and described above with respect to FIG. 1.

In certain embodiments, the method 240 includes a step 250 of synchronizing the system. As illustrated and described above with reference to FIG. 1, the patient may move their body (e.g., their head while wearing a headset), to manipulate the view of the patient. Changes made to the patient's view based on changes to the patient's head orientation and position changes are tracked using one or more sensors that store patient positioning data and update the patient scene in real-time with limited latency. This process is illustrated and described in further detail below with respect to FIG. 17.

FIG. 4 is a method flow chart of a method 270 for determining an effective vision correction and providing instructions for administering a treatment to a patient according to the vision correction.

The method 270 includes a step 272 of selecting one or more criteria for the simulation. The selection of criteria relate to one or more visual effects 410 (not shown), vision correction treatments 430 (not shown) and one or more ocular disorders 450 (not shown), which are illustrated and described in further detail with respect to FIGS. 6-15.

The method 270 includes a step 274 of providing the patient simulation to the patient. A process for providing the patient simulation to the patient is illustrated and described above with reference to FIG. 1, where a controller application 118 generates the patient simulation in two dimensions and transmits the patient simulation to the simulator application 120 to be displayed in three dimensions on a patient display 130 worn by the patient.

The method 270 includes a step 276 of receiving patient feedback. As illustrated and described above with reference to FIG. 1, the controller application 118 and the simulator application 120 are synchronized such that changes made to the simulation by the clinical care provider are viewed by the patient in real time on the patient display and movements by the patient are also shown to the clinical care provider in real time. As the clinical care provider provides the simulation to the patient that includes the selected criteria for the patient simulation, the patient may be asked one or more questions pertaining to what the patient is viewing in the simulation. In a non-limiting example, if the patient were to be evaluated for intraocular lens treatment, then the patient may initially see a blurry image that is representative of a simulation of a scene through a lens that contains cataracts. The clinical care provider may then select a new criterion to provide an intraocular lens filter to show the patient what a vision correction for the cataracts would look like if the intraocular lens were implanted during a surgical procedure. The patient may then provide feedback to the clinical care provider that expresses whether the intraocular lens was effective or ineffective in treating the cataracts.

The method 270 includes a step 278 of determining whether appropriate vision correction. As discussed above, if the patient provides feedback that is positive, then the clinical care provider may determine the simulated treatment was effective in treating the patient's condition and proceed to step 280. If the patient provides feedback that is negative, or if the feedback is positive and a better result can still be achieved, then the clinical care provider can proceed by selecting new criteria for the simulation to provide a new treatment or a stronger degree of treatment in the simulation. In certain embodiments, the step 278 can be performed automatically by the system 100 by receiving feedback, determining the effectiveness of a treatment, and selecting new criteria for the simulation.

The method 270 includes a step 280 of providing instructions for administering a treatment to a patient according to the vision correction. In a non-limiting example, if a patient with cataracts requires an IOL, and it was determined that an IOL of a certain degree is effective, then step 280 may include providing instructions to the clinical care provider recommending a procedure to implant an IOL at the determined degree of effectiveness.

In certain embodiments, and by non-limiting example, providing instructions for administering a treatment to a patient can include at least one of providing prescription eyeglasses, providing contact lenses, providing a low vision aid (e.g., a magnifying lens), providing vision therapy, providing a surgical procedure, and providing adjustments or repairs to eyeglasses. The surgical procedures can include, by non-limiting example, LASIK, photorefractive keratectomy, cataract surgery, glaucoma surgery, corneal transplant, retinal surgery, refractive lens exchange, laser trabeculoplasty, pterygium surgery, and strabismus surgery.

Figure 6:
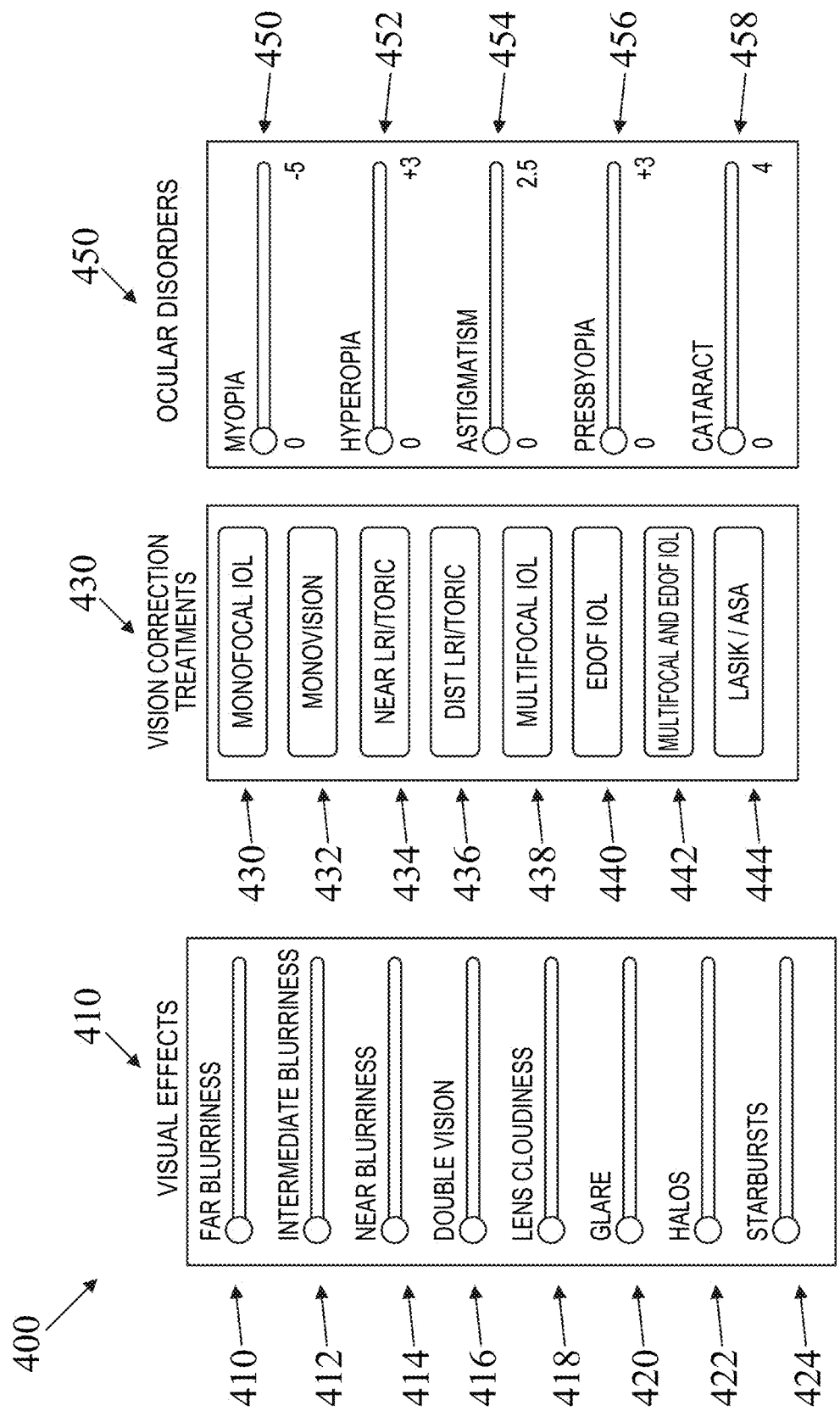
FIG. 6 is a schematic of a graphical user interface displaying options to a user to adjust one or more settings for the patient simulation in the controller application, according to one embodiment of the present disclosure.

FIG. 6 is a schematic of a graphical user interface 400 displaying options to a user to adjust one or more settings for the patient simulation in the controller application 118, according to one embodiment of the present disclosure.

The graphical user interface 400 shows options for adjusting one or more visual effects 410, vision correction treatments 430, and ocular disorders 450 (also referred to as the "settings"). These settings can be adjusted by a clinical care provider using the controller application 118. When the settings are adjusted, the adjustments are transmitted to the simulator application 120 and provided to a patient that is viewing them using the patient display 130. In certain embodiments, the settings can be adjusted based on an evaluation of patient data to provide one or more visual effects 410, vision correction treatments 430, and ocular disorders 450 that uniquely relate to a patient's condition. In certain embodiments, the adjustment of the settings based on patient data is performed automatically as the patient simulation is provided to the patient.

In certain embodiments, and as illustrated in further detail with respect to FIGS. 11-14, the one or more vision correction treatments 430 can include one or more filters. The filters may include a polarizing filter, an anti-reflective filter, or another filter for illustrating a visual effect 410, a vision correction treatment 430, or an ocular disorder 450. The filters shown are illustrative and are not limited to a polarizing filter or an anti-reflective filter as shown.

In certain embodiments, a degree of the settings can be adjusted to strengthen or weaken their effects. The adjustment of the degree of the settings can include a toggle for activating or inactivating one or more settings. Furthermore, the adjustment can include an adjustment icon for adjusting the degree of the setting between a minimum degree (i.e., where the setting is inactivated) and a maximum degree (i.e., when the setting is activated at its greatest intensity). In certain embodiments, the adjustment icon includes a slidable adjustment for horizontally translating the adjuster from a first side (representing the minimum degree) to a second side (representing the maximum degree). Although a horizontally translating adjustment icon is shown, the adjustment icon can include a vertical adjustment or any other adjustment mechanism as recognizable by one of ordinary skill in the art.

In certain embodiments, the visual effects 410 may include at least one of blurred images 411, 412, 414, double vision 416, lens cloudiness 418, glare 420, halos 422, and starbursts 424. The blurred images 411, 412, 414 include a far blur 411 (i.e., objects at a distance positioned far away from the camera or viewing point of the simulation will appear blurred), an intermediate blur 412 (i.e., objects at a distance positioned at an intermediate distance from the camera or viewing point of the simulation will appear blurred), and a near blur 414 (i.e., objects at a distance positioned close to the camera or viewing point of the simulation will appear blurred). In certain embodiments, the controller application 118 can include an adjustment for adjusting the distance of the blur between one or more of the far blur 411, the intermediate blur 412, and the near blur 414. In certain embodiments, the adjustment can include a sliding bar for adjustment between the far blur 411, the intermediate blur 412, and the near blur 414. It may be desirable to introduce one or more visual effects 410 to the patient simulation to educate patients on one or more effects they experience in their vision and how it can be corrected. The visual effects 410 are illustrated and described in further detail with respect to FIGS. 7-15.

The vision correction treatments 430 include at least one of a monofocal IOL 431, monovision 432, an astigmatism correction 434, 436, 438, an extended depth of focus IOL 440, an extended depth of focus and multifocal IOL 442, and a refractive surgery technique 444. The astigmatism correction includes at least one of a near astigmatism correction 434, a far astigmatism correction 436, and a multifocal IOL 438. It may be desirable to provide a simulation that simulates the effects of one or more correction treatments to help a patient decide whether to pursue one or more treatments for improving their vision. The effects of the vision correction treatments 430 are described below.

The monofocal IOL 431 is used in cataract surgery to replace the eye's natural lens. It corrects vision for one specific distance, typically either near or far, but not both simultaneously.

A monovision 432 correction is a technique used in vision correction surgeries or with contact lenses where one eye is corrected for near vision and the other for distance vision. This allows individuals to see clearly at both distances without the need for reading glasses.

Astigmatism correction 434, 436, 438 aims to improve vision by altering the shape of the cornea or by using specialized lenses to correct irregularities in the eye that cause distorted vision at various distances. This correction helps to achieve clearer and sharper vision overall at one or more distances. The multifocal IOL lens 438 is designed to provide clear vision at multiple distances (near, intermediate, and far) simultaneously, reducing the dependency on glasses or contact lenses after cataract surgery or lens replacement.

The extended depth of focus IOL 440 is designed to provide a continuous range of vision from near to intermediate distances, minimizing the need for reading glasses while maintaining good distance vision. It achieves this by elongating the focal point, enhancing visual quality across a broader range compared to traditional monofocal lenses.

The multifocal and EDOF IOL 442 is a type of multifocal lens that corrects vision at multiple distances (near, intermediate, and far), providing a continuous range of clear vision. It incorporates an advanced diffractive echelette design to extend depth of focus and reduce the need for glasses or contact lenses after cataract surgery.

LASIK (Laser-Assisted in situ Keratomileusis) and ASA (Advanced Surface Ablation) 444 are both types of refractive surgery used to correct vision by reshaping the cornea. LASIK involves creating a flap in the cornea and using a laser to reshape it, while ASA reshapes the cornea's surface directly without creating a flap, offering options for different types of vision correction needs.

Examples of ocular disorders 450 that can be shown within a patient simulation to a patient include, for example, myopia 451, hyperopia 452, astigmatism 454, presbyopia 456, and a cataract 458.

Myopia (commonly known as nearsightedness) is a refractive error where distant objects appear blurry, requiring close objects to be seen clearly. Hyperopia (or farsightedness) causes difficulty seeing up-close objects clearly, often requiring correction for both near and far vision. Astigmatism results from an irregularly shaped cornea or lens, causing distorted or blurry vision at any distance. Presbyopia is an age-related condition where the eye's lens loses flexibility, making it challenging to focus on close-up objects.

These conditions are important to treat because they can significantly impact daily life and quality of vision. Uncorrected emmetropia, myopia, hyperopia, and astigmatism can lead to eyestrain, headaches, and difficulty performing tasks such as reading or driving. Presbyopia affects nearly everyone over a certain age and necessitates reading glasses or multifocal lenses for clear near vision. Cataracts involve clouding of the eye's natural lens, causing gradual vision loss that can impair activities and eventually require surgical intervention to restore clear vision. Another example of the one or more settings being implemented on a graphical user interface of the controller application 118 is illustrated and described with respect to FIG. 15.

Figure 7:
FIG. 7 is a perspective view of an example simulation generated by the patient simulation system of FIGS. 1 and 6 that illustrates blurring of objects at a far distance from a user, according to one embodiment of the present disclosure.

FIG. 7 is a perspective view of an example simulation 500 generated by the patient simulation system 100 of FIGS. 1 and 6 that illustrates blurring of objects at a far distance from a user, according to one embodiment of the present disclosure.

The example simulation 500 includes a common setting (e.g., a kitchen table positioned within a home). A camera (i.e., a viewpoint of the patient) is positioned within the setting (e.g., at an end of the kitchen table). The example simulation 500 includes a near object 502 positioned close to the camera (e.g., a mobile phone). The example simulation 500 includes an intermediate object 504 (e.g., a laptop computer) positioned at an intermediate distance from the camera. The example simulation 500 includes far object 506 (e.g., a visual acuity chart) positioned at a far distance from the camera. As illustrated in the example simulation, the far object 506 is blurred, which correlates to a selection of a far blur 411 in the controller application 118 as illustrated and described in further detail above with respect to FIG. 6.

Figure 8:
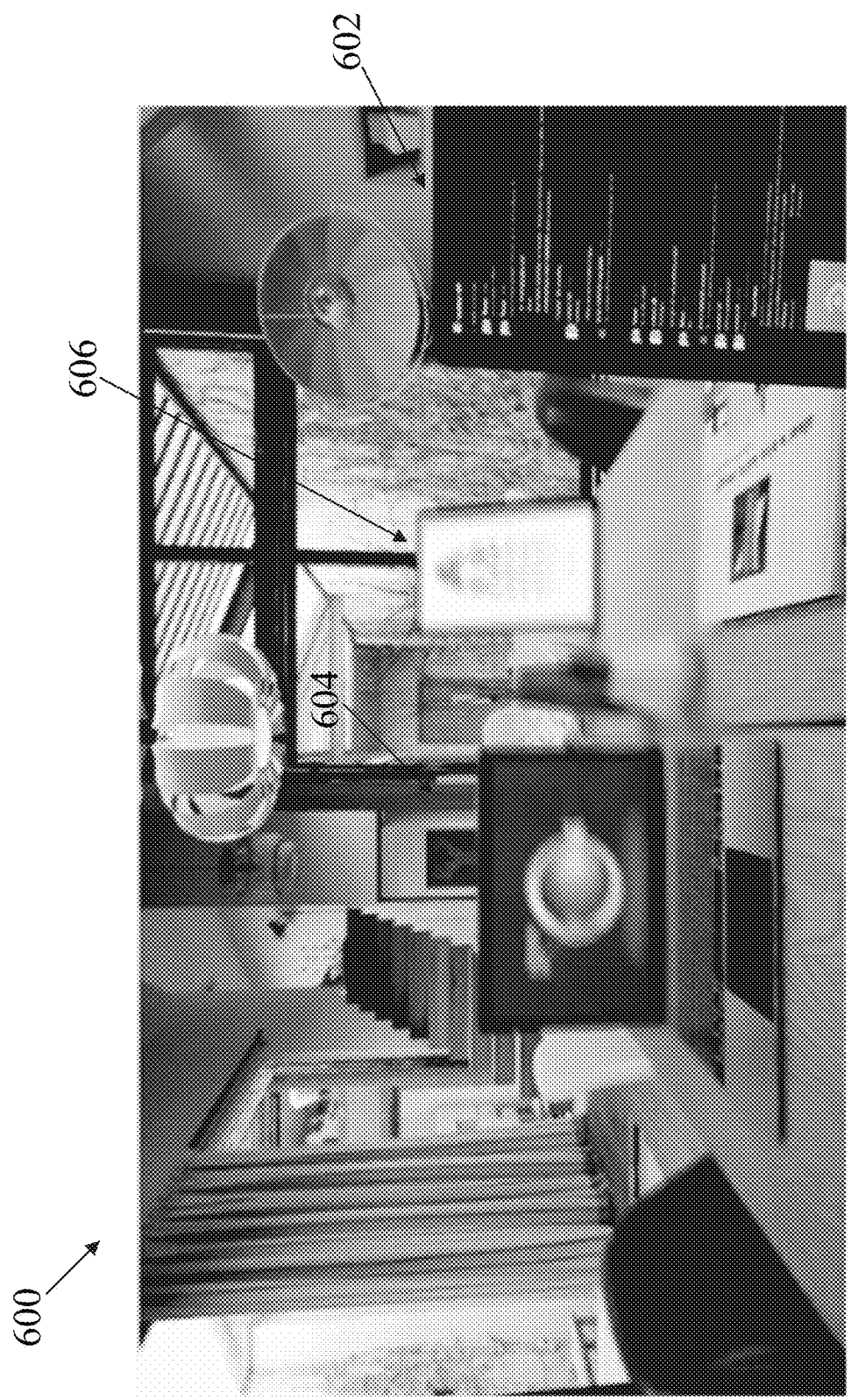
FIG. 8 is a perspective view of an example simulation generated by the patient simulation system of FIGS. 1 and 6 that illustrates blurring of objects at an intermediate distance from a user, according to one embodiment of the present disclosure.

FIG. 8 is a perspective view of an example simulation generated by the patient simulation system 100 of FIGS. 1 and 6 that illustrates blurring of objects at an intermediate distance from a user, according to one embodiment of the present disclosure.

The example simulation 600 includes a common setting like the setting shown in FIG. 7. The example simulation 600 includes a near object 602 positioned close to the camera (e.g., a mobile phone). The example simulation 600 includes an intermediate object 604 (e.g., a laptop computer) positioned at an intermediate distance from the camera. The example simulation 600 includes far object 606 (e.g., a visual acuity chart) positioned at a far distance from the camera. As illustrated in the example simulation, the intermediate object 604 is blurred, which correlates to a selection of an intermediate blur 412 in the controller application 118 as illustrated and described in further detail above with respect to FIG. 6.

Figure 9:
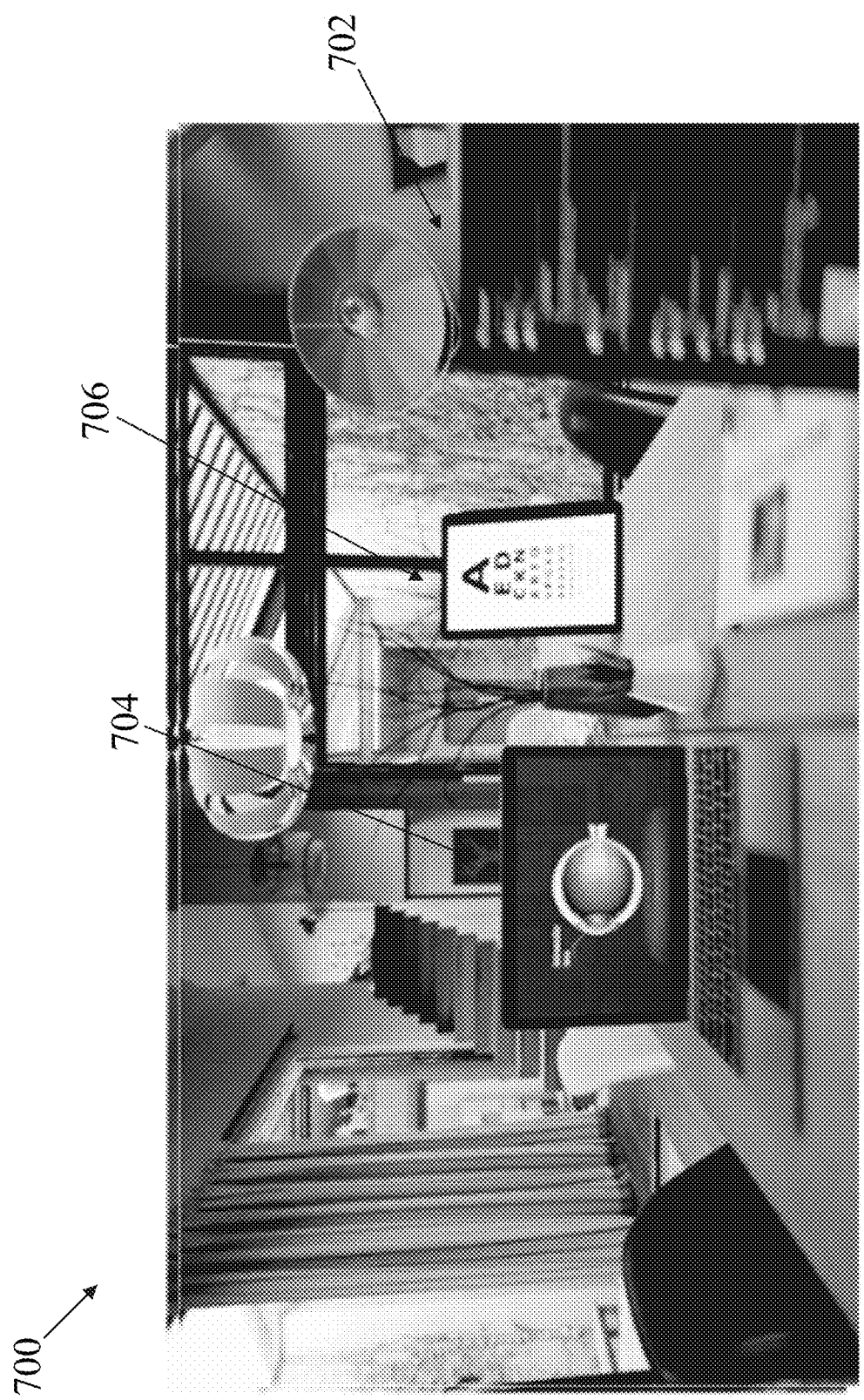
FIG. 9 is a perspective view of an example simulation generated by the patient simulation system of FIGS. 1 and 6 that illustrates blurring of objects at a near distance from a user, according to one embodiment of the present disclosure.

FIG. 9 is a perspective view of an example simulation generated by the patient simulation system 100 of FIGS. 1 and 6 that illustrates blurring of objects at a near distance from a user, according to one embodiment of the present disclosure.

The example simulation 700 includes a common setting like the setting shown in FIGS. 7-8. The example simulation 700 includes a near object 702 positioned close to the camera (e.g., a mobile phone). The example simulation includes an intermediate object 704 (e.g., a laptop computer) positioned at an intermediate distance from the camera. The example simulation 700 includes far object 706 (e.g., a visual acuity chart) positioned at a far distance from the camera. As illustrated in the example simulation 700, the near object 702 is blurred, which correlates to a selection of a near blur 414 in the controller application 118 as illustrated and described in further detail above with respect to FIG. 6.

Figure 10:
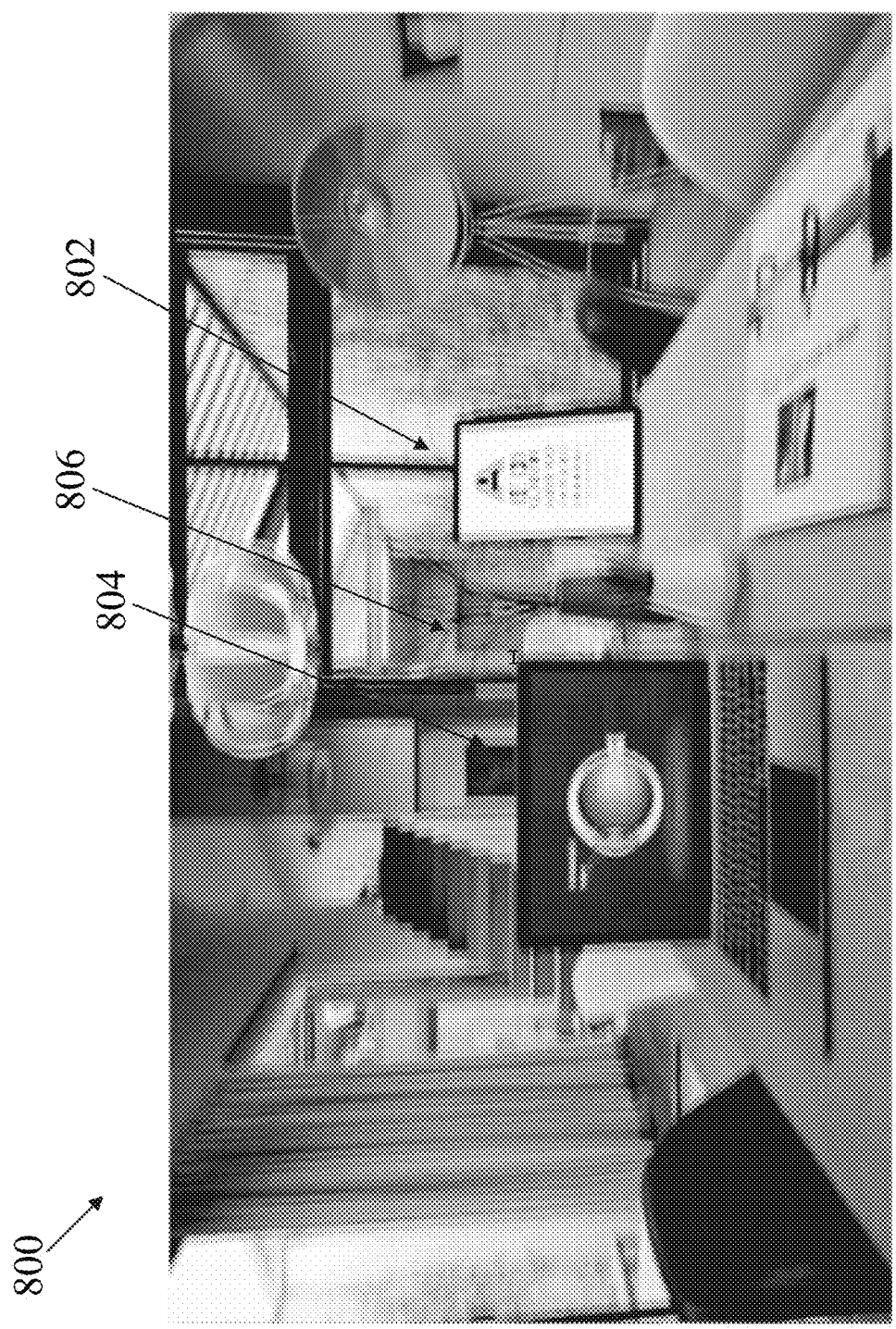
FIG. 10 is a perspective view of an example simulation generated by the patient simulation system of FIGS. 1 and 6 that illustrates double vision, according to one embodiment of the present disclosure.

FIG. 10 is a perspective view of an example simulation 800 generated by the patient simulation system 100 of FIGS. 1 and 6 that illustrates double vision, according to one embodiment of the present disclosure.

The example simulation 800 includes a common setting like the setting shown in FIGS. 7-9. The example simulation 800 includes a near object 802 positioned close to the camera (e.g., a mobile phone). The example simulation includes an intermediate object 804 (e.g., a laptop computer) positioned at an intermediate distance from the camera. The example simulation 800 includes far object 806 (e.g., a visual acuity chart) positioned at a far distance from the camera. As illustrated in the example simulation 800, the near object 802, the intermediate object 804, and the far object 806 are shown with double vision, which is a form of filter used to duplicate one or more of the objects 802, 804, 806 and offset them in a certain direction.

Figure 11:
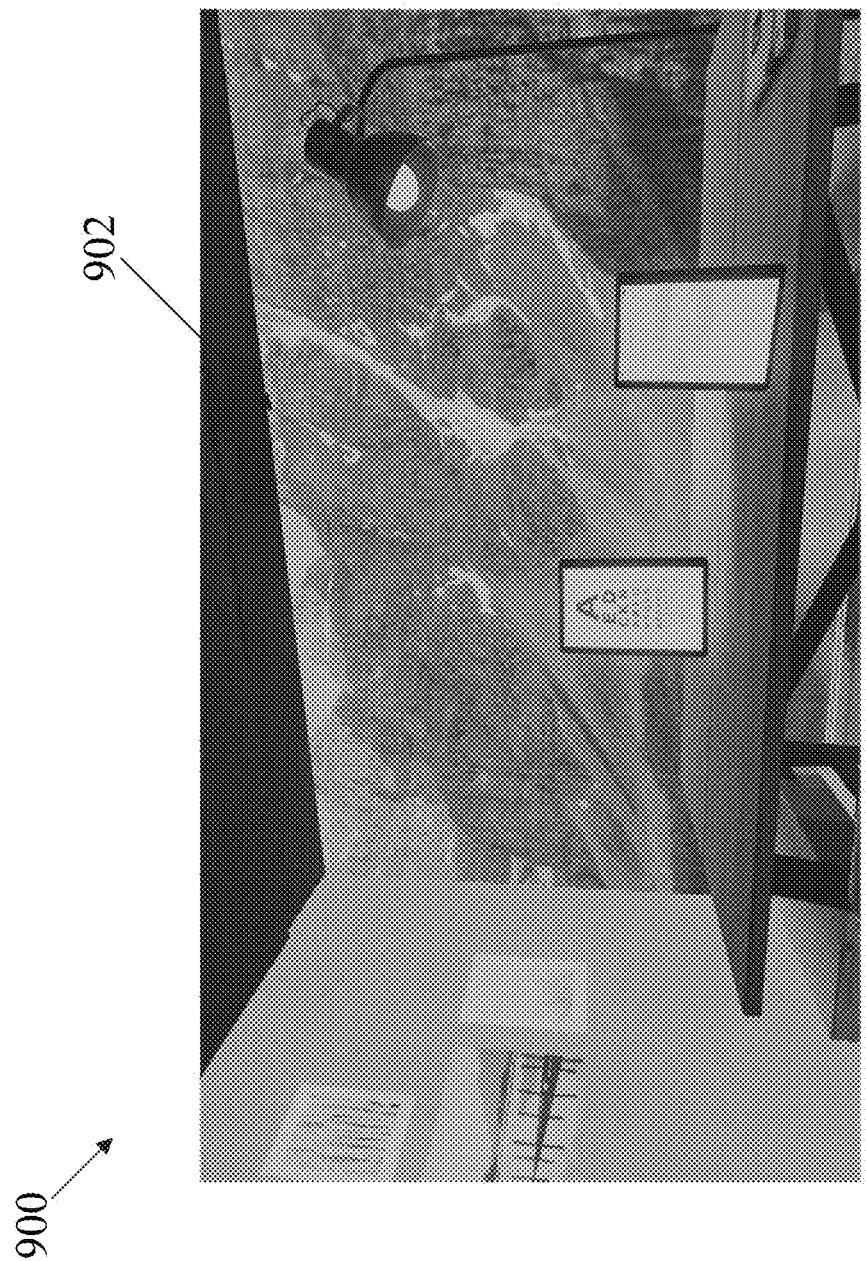
FIG. 11 is a perspective view of an example simulation generated by the patient simulation system of FIGS. 1 and 6 that illustrates lens cloudiness, according to one embodiment of the present disclosure.

FIG. 11 is a perspective view of an example simulation 900 generated by the patient simulation system 100 of FIGS. 1 and 6 that illustrates lens cloudiness, according to one embodiment of the present disclosure.

The example simulation 900 includes a common setting. In some embodiments, and as shown in FIG. 11 by non-limiting example, the common setting includes a room having a desk, a lamp, and one or more objects positioned on the desk. In some embodiments, the example simulation 900 includes a filter 902 having a colored and opaque film rendered over the camera to illustrate lens cloudiness 418, which correlates to a selection of the lens cloudiness 418 in the controller application 118 as illustrated and described in further detail above with respect to FIG. 6.

Figure 12:
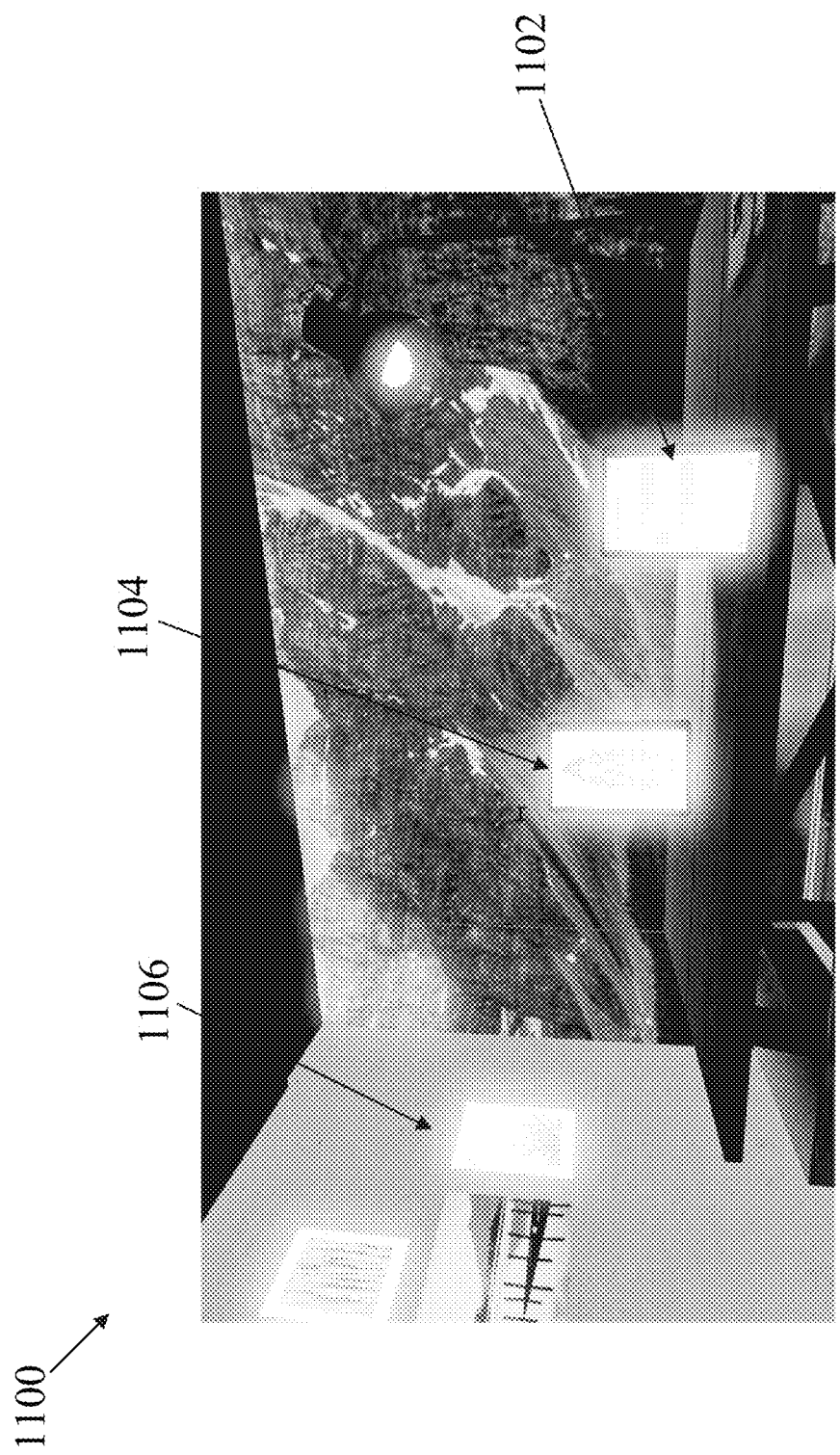
FIG. 12 is a perspective view of an example simulation generated by the patient simulation system of FIGS. 1 and 6 that illustrates one or more glares, according to one embodiment of the present disclosure.

FIG. 12 is a perspective view of an example simulation generated by the patient simulation system 100 of FIGS. 1 and 6 that illustrates one or more glares, according to one embodiment of the present disclosure.

The example simulation 1100 includes a common setting including a desk with one or more objects positioned on the desk. In some embodiments, the example simulation 1100 includes a camera filter and a mesh cover over one or more objects (such as a near object 1102, an intermediate object 1104, and a far object 1106) to operate over the camera's output. In certain embodiments, the glare filter is created by locating a source of light and offsetting and/or diffusing the source of light of adjacent pixels to create a glowing effect. Further, the glare filter may be adjusted by the controller application 118 to adjust the intensity of the pixels that are brightened to make them appear luminous, which enhances the overall light diffusion effect. The overall glare effect correlates to a selection of glare 420 in the controller application 118 as illustrated and described in further detail above with respect to FIG. 6.

Figure 13:
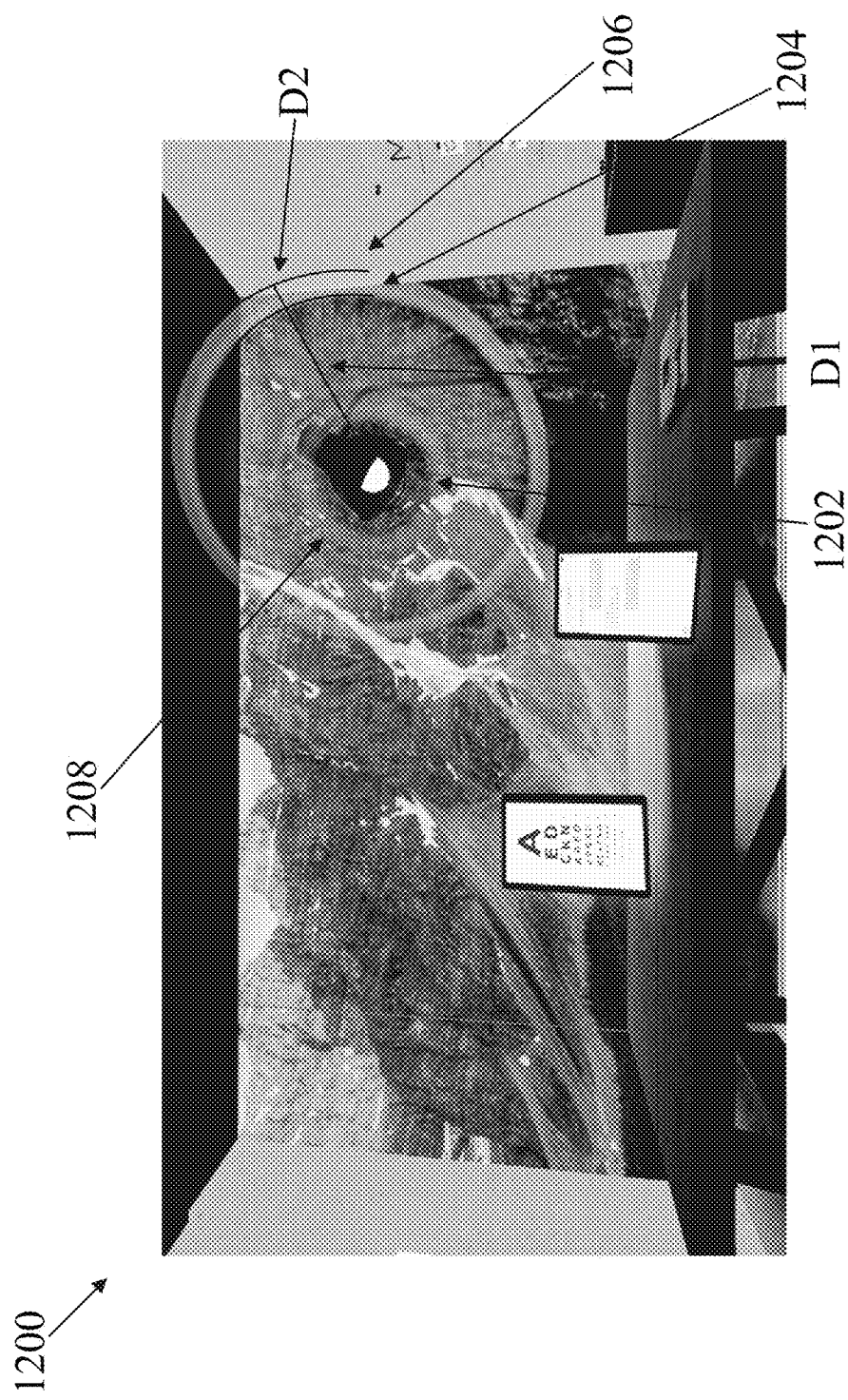
FIG. 13 is a perspective view of an example simulation generated by the patient simulation system of FIGS. 1 and 6 that illustrates one or more halos, according to one embodiment of the present disclosure.

FIG. 13 is a perspective view of an example simulation 1200 generated by the patient simulation system 100 of FIGS. 1 and 6 that illustrates one or more halos, according to one embodiment of the present disclosure.

The example simulation 1200 includes a common setting of a perspective of a person seated at a table or desk. The example simulation 1200 shows a halo effect 1202 (an outer ring) coming from a lamp 1208. The halo effect 1202 is generated by positioning a mesh over a lit object, such as the lamp 1208. The mesh consists of multiple circulars meshes that can be modified to include different sizes, different numbers of halos, and different lighting intensities. As shown with the halo effect 1202, one or more circular meshes can include any number of halo effects, such as a second halo effect 1204 and a third halo effect 1206 (illustrated by a curvature along a portion of the circumference of the halo effects 1204, 1206) having different diameters D1, D2 from the center of the light source. The overall halo effect correlates to a selection of a halo 422 in the controller application 118 as illustrated and described in further detail above with respect to FIG. 6.

Figure 14:
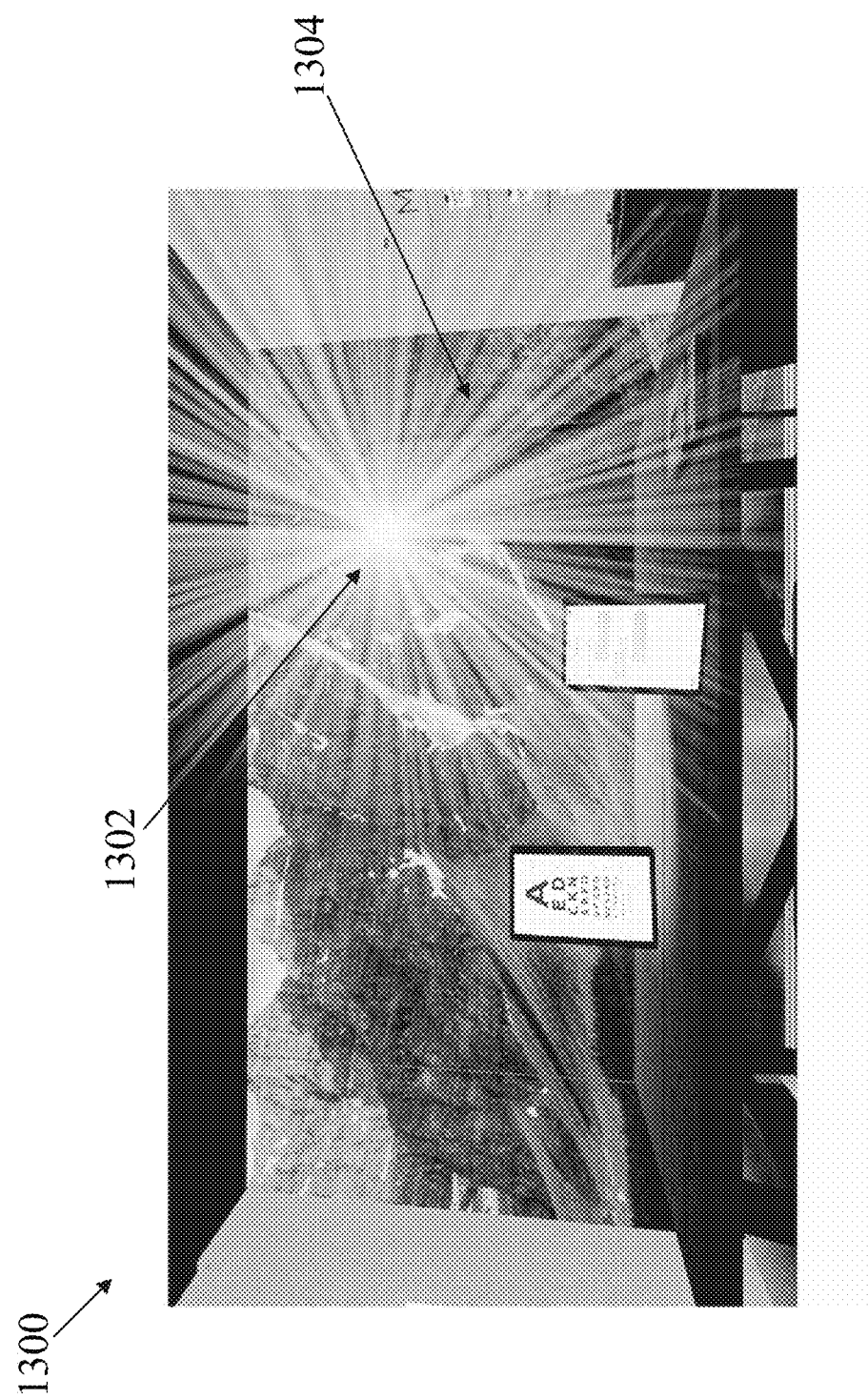
FIG. 14 is a perspective view of an example simulation generated by the patient simulation system of FIGS. 1 and 6 that illustrates one or more starbursts, according to one embodiment of the present disclosure.

FIG. 14 is a perspective view of an example simulation 1300 generated by the patient simulation system 100 of FIGS. 1 and 6 that illustrates one or more starbursts 424, according to one embodiment of the present disclosure. The starburst 424 is created by positioning a mesh over a lit object having multiple two-dimensional shaped meshes that can be modified by length, number of starbursts, light intensity, and rotation of the light source to generate the starburst effect. As shown in FIG. 14, the overall starburst effect 1302 from a lamp 1304 correlates to a selection of starburst 424 in the controller application 118 as illustrated and described in further detail above with respect to FIG. 6.

Figure 15:
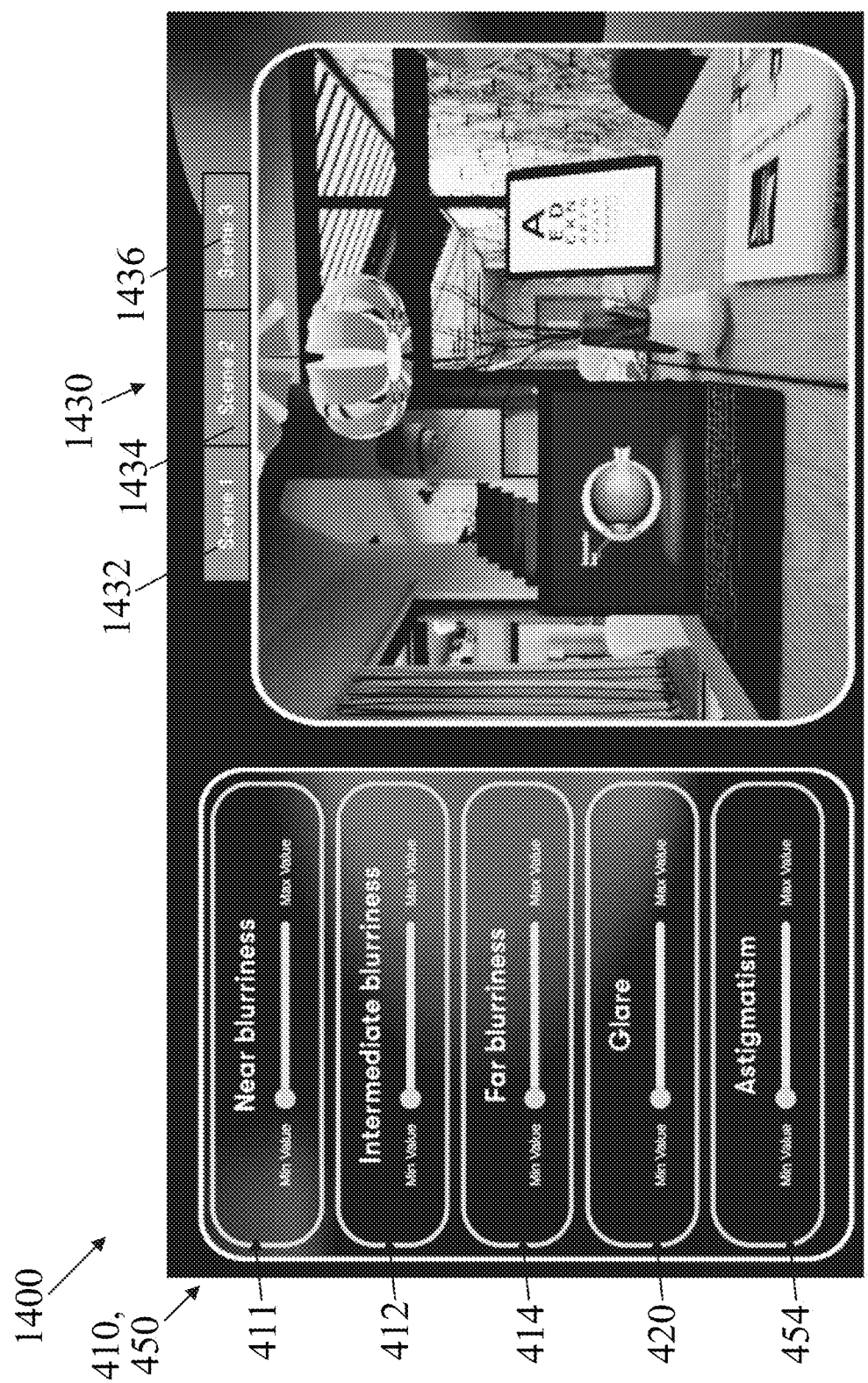
FIG. 15 is another schematic of a graphical user interface displaying options to a user to adjust a patient display by adjusting one or more visual effects and one or more scenes, according to one embodiment of the present disclosure.

FIG. 15 is another schematic of a graphical user interface 1400 displaying options to a user to adjust a patient display by adjusting one or more visual effects 410 and/or ocular disorder 450 and one or more scenes 1430, according to one embodiment of the present disclosure.

The graphical user interface shows an adjustment icon within each of the one or more visual effects 410 and/or ocular disorders 450 like the one illustrated and described above with respect to FIG. 6. In the exemplary graphical user interface 1400, the one or more visual effects 410 and/or ocular disorders include the near blur 411, the intermediate blur 412, the far blur 414, the glare 420, and astigmatism 454. These settings can be adjusted within each scene 1420 to illustrate one or more visual effects 410 or corrections for an ocular disorder 450.

The graphical user interface 1400 includes a scene selection feature 1430 with one or more icons for selecting one or more scenes. In certain embodiments, the scenes are preloaded in the patient simulation system memory 114 and the patient display memory 134 for the purpose of limiting a required transfer of data over the data transfer mechanism 140. As illustrated in FIG. 15, the scene selection feature 1430 includes a first scene 1432, a second scene 1434, and a third scene 1436; however, the scene selection tool 1430 can include any number of scenes. As illustrated in FIG. 15, the first scene 1432 is like what is shown in FIGS. 7-10.

Figure 16:
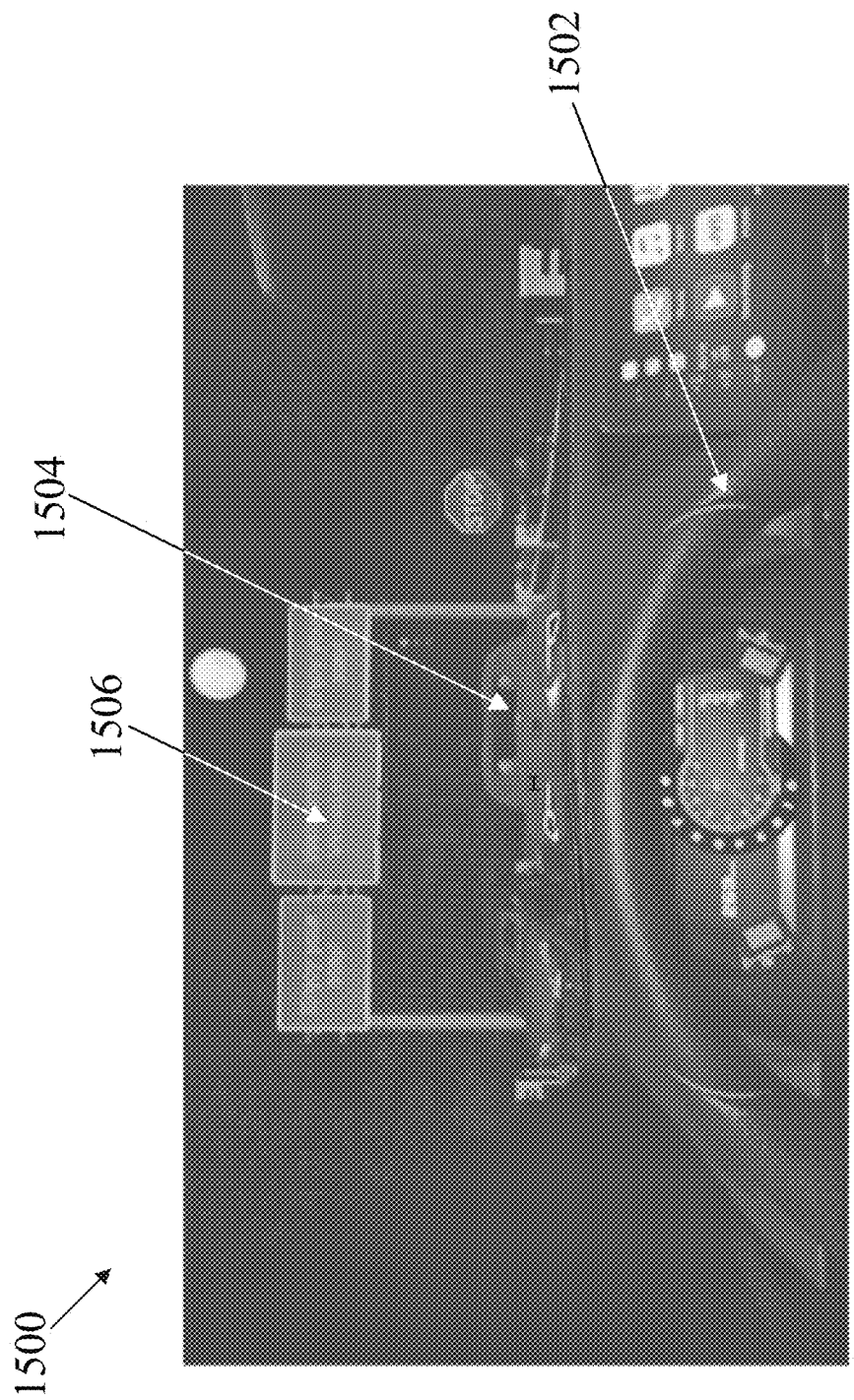
FIG. 16 is a perspective view of an example simulation generated by the patient simulation system of FIGS. 1 and 6 that illustrates a dynamic scene of a user driving a motor vehicle, according to one embodiment of the present disclosure.

FIG. 16 is a perspective view of an example simulation 1500 generated by the patient simulation system of FIGS. 1 and 6 that illustrates a dynamic scene 1500 of a user driving a motor vehicle, according to one embodiment of the present disclosure. The dynamic scene 1500 includes a camera that is viewing objects that are moving relative to the camera. In a non-limiting example, and as shown in FIG. 16, the camera is positioned within a user's vehicle 1502. The user's vehicle is traveling along a roadway where a second vehicle 1504 and a sign 1506 are positioned in front of the user's vehicle 1502. As the user's vehicle travels forward, the sign 1506 appears to travel toward the camera. Thus, the sign 1506 is an example of a dynamic object (i.e., an object that moves relative to the camera). Further, as the user's vehicle travels forward, the second vehicle 1504 travels at approximately the same velocity as the user's vehicle 1502. Thus, the second vehicle 1504 is an example of a static object (i.e., an object that does not move relative to the camera). However, if the second vehicle 1504 moves at a velocity that is not equal to the user's vehicle 1502, then a distance between the second vehicle 1504 and the user's vehicle 1502 would change, and this would make the second vehicle 1504 move relative to the user's vehicle 1502 as a dynamic object.

Figure 17:
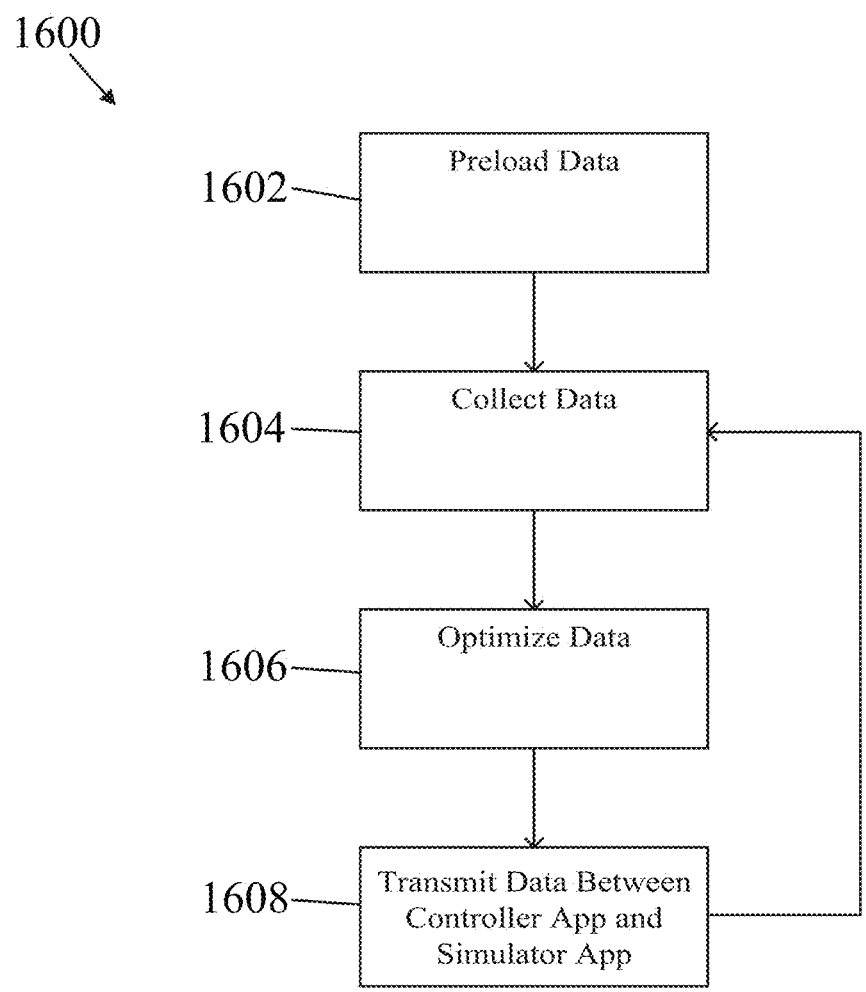
FIG. 17 is a method flow diagram of a method for streaming data from the patient simulation system 110 to the patient display 130, according to one embodiment of the present disclosure.

FIG. 17 is a method flow diagram of a method 1600 for streaming data between the patient simulation system 110 to the patient display 130, according to one embodiment of the present disclosure.

The method 1600 includes preloading data onto the patient display memory 134 and the patient simulation system memory 114. The preloaded data may include, by non-limiting example, patient data, scenes for the patient simulation, a patient display unique ID for connecting to the controller application 118, individual filter data (e.g., the name of the filter and any value(s) selected prior to initiating the patient simulation), and any other predetermined inputs from the controller application 118 and the simulator application 120 prior to initializing the patient simulation. Preloading data limits the amount of data that is required to be transferred between the patient simulation system 110 and the patient display 130 to improve the speed at which the system 100 operates while reducing latency.

The method 1600 includes a step 1604 of collecting data. As illustrated and described above with respect to FIGS. 1-3, positional data (e.g., the patient's body movements while viewing the simulation) can be collected by using one or more sensors attached to the patient display.

The method 1600 includes a step 1606 of optimizing the data. This may include, by non-limiting example, packaging positional data relating to a position and orientation of the patient display 130 into small data packets that are transmitted from the simulator application 120 to the controller application 118 at high frequencies. This may include, by non-limiting example, utilizing one or more data compression algorithms to reduce the size of data packets transmitted between the controller application 118 and simulator application 120, which minimizes the amount of bandwidth required and speeds up the transfer process.

The method 1600 includes a step 1608 of transmitting data between the controller application 118 and the simulator application 120. The purpose of transmitting data between the controller application 118 and the simulator application 120 is to synchronize the applications such that the view on the controller application 118 is identical to the view in the simulator application 120 except for the controller application 118 displays the scene in two dimensions and the simulator application 120 displays the scene in three dimensions.

Furthermore, in certain embodiments, the synchronization of the applications may take place at many different points of time by reperforming steps 1604, 1606, and 1608. In certain embodiments, synchronization can occur at a predetermined refresh rate to ensure the controller application 118 and the simulator application 120 are displaying the same scene with minimal latency.

The method 1600 illustrates a technical effect for improving the functioning of a computer (e.g., the system 100) itself for the purposes of transmitting data between a patient simulation system 110 and a patient display 130 at improved rates for the purpose of improving an immersive experience of a patient display. In certain embodiments, the system 100 includes a patient simulation system 110 and a patient display 130 that include the controller application 118. The controller application 118 minimizes data (e.g., the controller data 122 and the simulator data 124) that is transferred between the patient simulation system 110 and the patient display 130 to reduce latency. Further, in certain embodiments, the system 100 minimizes latency and the transmission of data between the patient simulation system 110 and the patient display 130 by only transmitting changes generated within the controller application 118 to the patient display 130 and only returning changes in positional data and gyroscopic data from the patient display 130 to the patient simulation system 110.

CONCLUSION

The foregoing description of the exemplary embodiments has been presented only for the purposes of illustration and description is not intended to be exhaustive or to limit the compositions, systems, and methods herein to the precise forms disclosed. Many modifications and variations are possible considering the above teachings.

The embodiments were chosen and described to explain the principles of the technology discussed herein and their practical application to enable others skilled in the art to utilize the various embodiments and with various modifications as are suited to the particular use contemplated. Alternative embodiments will become apparent to those skilled in the art to which the present technologies pertain without departing from their spirit and scope.

What is claimed is:

1. A process for vision correction simulation comprising:
   receiving a selection of criteria for generating a patient simulation;
   generating a first set of instructions, via a controller application, for displaying a first view of the patient simulation corresponding to the selection of criteria to be viewed in two dimensions using a first simulator application;
   generating a second set of instructions, via the controller application, for displaying a second view of the patient simulation corresponding to the selection of criteria to be viewed in three dimensions using a second simulator application;
   transmitting the first set of instructions to the first simulator application and the second set of instructions to the second simulator application; and
   synchronizing the first view to the second view by tracking a position and head orientation of a patient;
   wherein:
      the first set of instructions and the second set of instructions include manipulation criteria for manipulating one or more visual scenes by applying one or more filters or manipulating a mesh cover applied to the one or more visual scenes;

the first view and the second view correspond to one or more visual scenes for displaying at least one of a visual effect, a vision correction treatment, and an ocular disorder;

the visual effect comprises at least one of clear images blurred images, double vision, lens cloudiness, glare, halos, and starbursts;

the vision correction treatment comprises at least one of a monofocal IOL, monovision, an astigmatism correction, an extended depth of focus IOL, a symphony IOL, a cataract, a multifocal IOL, a lens filter, an anti-reflective coating, an anti-glare feature, and a refractive surgery technique; and the ocular disorder comprises at least one of emmetropia, myopia, hyperopia, astigmatism, presbyopia, and cataracts.

2. The process of claim 1, further comprising a patient display for displaying the second view.

3. The process of claim 2, further comprising collecting positional data and gyroscopic data using the patient display.

4. The process of claim 3, further comprising transmitting the positional data and the gyroscopic data to the controller application.

5. The process of claim 2, wherein the patient display is configured to display the second view to a patient.

6. The process of claim 2, wherein the patient display comprises at least one of an AR headset, a VR headset, and an XR headset.

7. The process of claim 1, wherein the blurred images comprise at least one of a far blur, an intermediate blur, and a near blur.

8. The process of claim 1, wherein the astigmatism correction includes at least one of a near astigmatism correction or a far astigmatism correction.

9. The process of claim 1, further comprising applying one or more ocular disorders to the first view and the second view.

10. The process of claim 1, wherein the first simulator application and the second simulator application are identical applications installed on a patient simulation system and a patient display.

11. A process for displaying one or more visual scenes comprising:

receiving instructions for displaying the one or more visual scenes at a simulator application operating on a computing device from a controller application, wherein the instructions include one or more selections for the one or more visual scenes and manipulation criteria;

loading the one or more visual scenes for display according to the one or more selections for the one or more visual scenes;

manipulating the one or more visual scenes according to the manipulation criteria, wherein the manipulation criteria comprises at least one of applying one or more filters or manipulating a mesh applied to the one or more visual scenes; and displaying the one or more visual scenes in three dimensions;

wherein:

the one or more visual scenes comprise at least one of one or more visual effects, one or more vision correction treatments, and one or more ocular disorders;

the one or more visual effects comprise at least one of clear images, blurred images, double vision, lens cloudiness, glare, halos, and starbursts;

the one or more vision correction treatments comprises at least one of a monofocal IOL, monovision, an astigmatism correction, an extended depth of focus IOL, a cataract, a multifocal IOL, a lens filter, an anti-reflective coating, and an anti-glare feature; and the one or more ocular disorders comprises at least one of emmetropia, myopia, hyperopia, astigmatism, presbyopia, and cataracts.

12. The process of claim 11, wherein the one or more visual scenes comprise at least one of a static scene or a dynamic scene.

13. The process of claim 11, further comprising adjusting a degree of the one or more visual effects.

14. The process of claim 11, further comprising adjusting a degree of the one or more ocular disorders.

15. The process of claim 11, further comprising adjusting a degree of the one or more vision correction treatments.

16. The process of claim 11, further comprising:

transmitting gyroscopic data and positional data; and receiving subsequent instructions based on the gyroscopic data and the positional data.

17. A process for vision correction simulation comprising:

receiving a selection of criteria for generating a patient simulation;

generating a first set of instructions, via a controller application, for displaying a first view of the patient simulation corresponding to the selection of criteria to be viewed in two dimensions using a first simulator application;

generating a second set of instructions, via the controller application, for displaying a second view of the patient simulation corresponding to the selection of criteria to be viewed in three dimensions using a second simulator application;

transmitting the first set of instructions to the first simulator application and the second set of instructions to the second simulator application; and synchronizing the first view to the second view by tracking a position and head orientation of a patient;

wherein:

the first set of instructions and the second set of instructions include manipulation criteria for manipulating one or more visual scenes by applying one or more filters or manipulating a mesh applied to the one or more visual scenes; and the first view and the second view correspond to one or more visual scenes for displaying at least one of a visual effect, a vision correction treatment, and an ocular disorder.

18. The process of claim 17, wherein the visual effect further comprises at least one of clear images, blurred images, double vision, lens cloudiness, glare, halos, and starbursts.

19. The process of claim 17, wherein the vision correction treatment comprises at least one of a monofocal IOL, monovision, an astigmatism correction, an extended depth of focus IOL, a cataract, a multifocal IOL, a lens filter, an anti-reflective coating, and an anti-glare feature.

20. The process of claim 17, wherein the ocular disorder comprises at least one of emmetropia, myopia, hyperopia, astigmatism, presbyopia, and cataracts.

\* \* \* \* \*